United States Patent
Sorin et al.

(10) Patent No.: US 11,141,942 B2
(45) Date of Patent: Oct. 12, 2021

(54) MULTI-MATERIAL STRETCHABLE OPTICAL, ELECTRONIC AND OPTOELECTRONIC FIBERS AND RIBBONS COMPOSITES VIA THERMAL DRAWING

(71) Applicant: ECOLE POLYTECHNIQUE FEDERALE DE LAUSANNE (EPFL), Lausanne (CH)

(72) Inventors: Fabien Sorin, St-Sulpice (CH); Yunpeng Qu, Lausanne (CH); Marco Volpi, Etoy (CH); Wei Yan, Echandens-Denges (CH); Dang Tung Nguyen, Ecublens (CH); Alexis Page, Renens (CH)

(73) Assignee: ECOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 55 days.

(21) Appl. No.: 16/076,929

(22) PCT Filed: Feb. 10, 2017

(86) PCT No.: PCT/IB2017/050749
§ 371 (c)(1),
(2) Date: Aug. 9, 2018

(87) PCT Pub. No.: WO2017/137945
PCT Pub. Date: Aug. 17, 2017

(65) Prior Publication Data
US 2019/0047240 A1    Feb. 14, 2019

(30) Foreign Application Priority Data
Feb. 10, 2016   (EP) ..................................... 16155102

(51) Int. Cl.
*B29D 11/00* (2006.01)
*D01F 1/10* (2006.01)
(Continued)

(52) U.S. Cl.
CPC ........ *B29D 11/00721* (2013.01); *A61B 90/30* (2016.02); *A61L 31/022* (2013.01);
(Continued)

(58) Field of Classification Search
CPC ..... B21C 9/00; B29C 48/05; B29K 2105/256; C03B 23/037; C03B 37/0256;
(Continued)

(56) References Cited

U.S. PATENT DOCUMENTS 3,659,915 A    5/1972   Maurer et al.
4,426,420 A *  1/1984   Likhyani ................ D04H 1/492
                                                          28/103

(Continued)

FOREIGN PATENT DOCUMENTS

DE    32 44 778         6/1983
JP    H02074667 A       3/1990
(Continued)

OTHER PUBLICATIONS

International Search Report for PCT/IB2017/050749 dated May 22, 2017, 5 pages.
(Continued)

*Primary Examiner* — Camie S Thompson
(74) *Attorney, Agent, or Firm* — Nixon & Vanderhye P.C.

(57) ABSTRACT

The present invention concerns a thermal drawing method for forming fibers, wherein said fibers are made at least from a stretchable polymer. The present invention also concerns drawn fibers made by the process.

10 Claims, 16 Drawing Sheets

(51) Int. Cl.

| | | |
|---|---|---|
| *D01F 6/30* | (2006.01) | |
| *D01F 6/42* | (2006.01) | |
| *D01F 8/04* | (2006.01) | |
| *G02B 1/04* | (2006.01) | |
| *G02B 6/02* | (2006.01) | |
| *D01D 5/00* | (2006.01) | |
| *A61B 90/30* | (2016.01) | |
| *A61L 31/02* | (2006.01) | |
| *A61L 31/04* | (2006.01) | |
| *A61L 31/06* | (2006.01) | |
| *G01L 1/24* | (2006.01) | |
| *H01B 3/30* | (2006.01) | |
| *H01B 13/00* | (2006.01) | |
| *H02N 1/04* | (2006.01) | |
| *G02B 6/44* | (2006.01) | |

(52) U.S. Cl.
CPC ........... *A61L 31/024* (2013.01); *A61L 31/048* (2013.01); *A61L 31/06* (2013.01); *D01D 5/00* (2013.01); *D01F 1/10* (2013.01); *D01F 6/30* (2013.01); *D01F 6/42* (2013.01); *D01F 8/04* (2013.01); *G01L 1/242* (2013.01); *G02B 1/045* (2013.01); *G02B 6/02152* (2013.01); *H01B 3/30* (2013.01); *H01B 13/0013* (2013.01); *H02N 1/04* (2013.01); *A61B 2090/306* (2016.02); *G02B 6/4403* (2013.01); *G02B 6/4416* (2013.01)

(58) Field of Classification Search
CPC ... C03B 37/026; C03B 23/25; H01B 13/0013; H01B 3/30; H01B 13/0023; H01B 12/0013; Y10T 428/2929; Y10T 428/24273; D01F 1/10; D01D 5/00; D01D 5/253; A61B 2090/306; B29D 11/00721; G01L 1/242; G01L 1/20
USPC .......................................... 264/164; 428/373
See application file for complete search history.

(56) References Cited

U.S. PATENT DOCUMENTS

| | | | |
|---|---|---|---|
| 4,504,300 | A | 3/1985 | Gauthier et al. |
| 5,984,747 | A | 11/1999 | Bhagavatula et al. |
| 7,292,758 | B2 | 11/2007 | Bayindir et al. |
| 7,295,734 | B2 | 11/2007 | Bayindir et al. |
| 10,704,167 | B2 | 7/2020 | Sorin et al. |
| 2003/0001082 | A1 | 1/2003 | Duncan et al. |
| 2005/0286847 | A1 | 12/2005 | Arimondi et al. |
| 2010/0221969 | A1* | 9/2010 | Chen .................. D01F 1/10 442/189 |
| 2010/0290781 | A1 | 11/2010 | Overton et al. |
| 2011/0123162 | A1 | 5/2011 | Molin et al. |
| 2012/0027987 | A1 | 2/2012 | Poulakis |
| 2012/0301093 | A1 | 11/2012 | Sillard et al. |
| 2013/0202888 | A1 | 8/2013 | Abouraddy et al. |
| 2016/0270388 | A1 | 9/2016 | Lai et al. |
| 2018/0003859 | A1 | 1/2018 | Morasse |
| 2018/0088258 | A1 | 3/2018 | Yamamoto et al. |
| 2018/0327931 | A1 | 11/2018 | Sorin et al. |

FOREIGN PATENT DOCUMENTS

| | | |
|---|---|---|
| KR | 2012-0129040 | 11/2012 |
| WO | 2008057431 A2 | 5/2008 |
| WO | 2012/112198 | 8/2012 |
| WO | 2014/047660 | 3/2014 |
| WO | 2014/130917 | 8/2014 |
| WO | 2017085323 A1 | 5/2017 |

OTHER PUBLICATIONS

Written Opinion of the ISA for PCT/IB2017/050749 dated May 22, 2017, 8 pages.
Abouraddy, A. F., et al., "Towards multimaterial multifunctional fibres that see, hear, sense and communicate," Nature Materials, vol. 6, May 2007, pp. 336-347.
Albella, Pablo, et al., "Electric and Magnetic Field Enhancement with Ultralow Heat Radiation Dielectric Nanoantennas: Considerations for Surface-Enhanced Spectroscopies," ACS Photonics, vol. 1, 2014, pp. 524-529.
Arbabi, Amir, et al., "Dielectric metasurfaces for complete control of phase and polarization with subwavelength spatial resolution and high transmission," Nature Nanotechnology, vol. 10, 2015, 9 pages.
Arbabi, Ehsan, et al., "MEMS-tunable dielectric metasurface lens," Nature Communications, vol. 9, 2018, 9 pages.
Backholm, Matilda, et al., "Capillary levelling of a cylindrical hole in a viscous film," Soft Matter, vol. 10, 2014, pp. 2550-2558.
Banaei, Esmaeil-Hooman, et al., "Design of a polymer optical fiber luminescent solar concentrator," Progress in Photovoltaics: Research and Applications, vol. 23, 2015, pp. 403-416.
Bontempi, Nicolò, et al., "Highly sensitive biosensors based on all-dielectric nanoresonators," Nanoscale, vol. 9, 2017, pp. 4972-4980.
Brudieu, Barbara, et al., "Sol-Gel Route Toward Efficient and Robust Distributed Bragg Reflectors for Light Management Applications," Advanced Optical Materials, vol. 2, 2014, 8 pages.
Cho, Youngtae, et al., "Development of large area nano imprint technology by step and repeat process and pattern stitching technique," Microelectronic Engineering, vol. 86, 2009, pp. 2417-2422.
De Gennes, Pierre-Gilles, et al., "Capillarity and Wetting Phenomena: Drops, Bubbles, Pearls, Waves," Springer Science & Business Media, 2003, 14 pages.
Decker, Manuel, et al., "High-efficiency light-wave control with all-dielectric optical Huygens' metasurfaces," Advanced Optical Materials, vol. 3, 17 pages.
Deng, D. S., et al., "Exploration of in-fiber nanostructures from capillary instability," Optics Express, vol. 19, No. 17, Aug. 15, 2011, pp. 16273-16290.
Eggleton, Benjamin J., et al., "Chalcogenide photonics," Nature Photonics, vol. 5, Mar. 2011, pp. 141-148.
Evlyukhin, Andrey B., et al., "Resonant lattice Kerker effect in metasurfaces with electric and magnetic optical responses," Laser & Photonics Reviews, vol. 11, 2017, 15 pages.
Fan, Jonathan A., et al., "Self-Assembled Plasmonic Nanoparticle Clusters," Science, vol. 328, May 28, 2010, pp. 1135-1138.
Flauraud, Valentin, et al., "Nanoscale topographical control of capillary assembly of nanoparticles," Nature Nanotechnology, vol. 12, Jan. 2017, 9 pages.
Gupta, T. Das, et al., "Ultrafine tuning of metal volume fraction in Silver/silicate nanocomposites near the percolation threshold," Nanoscale, vol. 9, 2017, 11 pages
Hosseini, Peiman, et al., "An optoelectronic framework enabled by low-dimensional phase-change films," Nature, vol. 511, Jul. 10, 2014, pp. 206-211.
Jahani, Saman, et al., "All-dielectric metamaterials," Nature Nanotechnology, vol. 11, Jan. 2016, pp. 23-36.
Kao, K. C., et al., "Dielectric-fibre suface waveguides for optical frequencies," IEE Proceedings, vol. 133, Pt. J, No. 3, 1986, pp. 191-198.
Khorasaninejad, Mohammadreza, et al., "Metalenses at visible wavelengths: Diffraction-limited focusing and subwavelength resolution imaging," Science, vol. 352, Issue 6290, Jun. 3, 2016, pp. 1190-1194.
Koenderink, A. Femius, et al., "Nanophotonics: Shrinking light-based technology," Science, vol. 348, Issue 6234, May 1, 2015, pp. 516-521.
Kohoutek, Tomas, et al., "Sub-micrometer soft lithography of a bulk chalcogenide glass," Optic Express, vol. 21, No. 8, Apr. 22, 2013, pp. 9584-9591.
Kuznetsov, Arseniy I., et al., "Optically resonant dielectric nanostructures," Science, vol. 354, Issue 6314, Nov. 18, 2016, 9 pages.

(56) References Cited

OTHER PUBLICATIONS

Le Bris, A., et al., "Self-organized ordered silver nanoparticle arrays obtained by solid state dewetting," Applied Physics Letters, vol. 105, 2014, pp. 203102-1-203102-5.
Li, Lan, et al., "Integrated flexible chalcogenide glass photonic devices," Nature Photonics, vol. 8, Aug. 2014, pp. 643-649.
Li, Lan, et al., "Monolithically integrated stretchable photonics," Light: Science & Applications, vol. 7, 2018, 8 pages.
Limonov, Mikhail F., et al., "Fano resonances in photonics," Nature Photonics, vol. 11, Sep. 2017, pp. 543-554.
Lin, Dianmin, et al., "Dielectric gradient metasurface optical elements," Science, vol. 345, Issue 6194, Jul. 18, 2014, pp. 298-302.
Lin, Qing-Yuan, et al., "Building superlattices from individual nanoparticles via template-confined DNA-mediated assembly," Science, vol. 359, Feb. 9, 2018, pp. 669-672.
Liu, Jin-gang, et al., "High refractive index polymers: fundamental research and practical applications," Journal of Materials Chemistry, vol. 19, 2009, pp. 8907-8919.
Liu, Sheng, et al., "Resonantly enhanced second-harmonic generation using III-V semiconductor all-dielectric metasurfaces," Nano Letters, vol. 16, 28 pages.
Maguid, Elhanan, et al., "Photonic spin-controlled multifunctional shared-aperture antenna array," Science, vol. 352, Issue 6290, 2016, 8 pages.
Ok, Jong G., et al., "A step toward next-generation nanoimprint lithography: extending productivity and applicability," Applied Physics A, vol. 121, 2015, pp. 343-356.
Oron, Alexander, et al., "Long-scale evolution of thin liquid films," Reviews of Modem Physics, vol. 69, No. 3, Jul. 1997, pp. 931-980.
Parry, Matthew, et al., "Active tuning of high-Q dielectric meta surfaces," Applied Physics Letters, vol. 111, 2017, pp. 053102-1-053102-4.
Rotenberg, N., et al., "Mapping nanoscale light fields," Nature Photonics, vol. 8, Dec. 2014, pp. 919-926.
Russell, Philip, "Photonic Crystal Fibers," Science, vol. 299, Jan. 17, 2003, pp. 358-362.
Schmidt, Markus Alexander, et al., "Hybrid Optical Fibers—An Innovative Platform for In-Fiber Photonic Devices," Advanced Optical Materials, vol. 4, 2016, pp. 13-36.
Sharma, Ashutosh, et al., "Pattern Formation in Unstable Thin Liquid Films," Physical Review Letters, vol. 81, No. 16, Oct. 19, 1998, pp. 3463-3466.
She, Alan, et al., "Adaptive metalenses with simultaneous electrical control of focal length, astigmatism, and shift," Science Advances, vol. 4, Feb. 23, 2018, 7 pages.
Solmaz, M., et al., "Patterning chalcogenide glass by direct resist-free thermal nanoimprint," Journal of Vacuum Science & Technology B, vol. 26, No. 2, Mar./Apr. 2008, pp. 606-610.
Stillwagon, L. E., et al., "Fundamentals of topographic substrate leveling," Journal of Applied Physics, vol. 63, No. 11, Jun. 1, 1988, pp. 5251-5258.
Style, Robert W., et al., "Surface tension and contact with soft elastic solids," Nature Communications, vol. 4, 2013, 6 pages.
Tao, Guangming, et al., "Multimaterial Fibers," International Journal of Applied Glass Science, vol. 3, No. 4, 2012, pp. 349-368.
Thompson, Carl V., "Solid-State Dewetting of Thin Films," Annual Review of Materials Research, vol. 42, 2012, 38 pages.
Tverjanovich, A. S., "Temperature Dependence of the Viscosity of Chalcogenide Glass-Forming Melts," Glass Physics and Chemistry, vol. 29, No. 6, 2003, pp. 532-536
Vigderman, Leonid, et al., "Functional Gold Nanorods: Synthesis, Self-Assembly, and Sensing Applications," Advanced Materials, vol. 24, 2012, pp. 4811-4841.

Volodin, Pylyp, et al., "Dewetting of thin polymer film on rough substrate: I. Theory," Journal of Physics D: Applied Physics, vol. 41, 2008, 11 pages.
Wang, Ken Xingze, et al., "Absorption Enhancement in Ultrathin Crystalline Silicon Solar Cells with Antireflection and Light-Trapping Nanocone Gratings," Nano Letters, vol. 12, 2012, pp. 1616-1619.
Wang, Lei, et al., "Nonlinear wavefront control with all-dielectric metasurfaces," Nano Letters, vol. 18, 2018, 20 pages.
Wang, Qian, et al., "Optically reconfigurable metasurfaces and photonic devices based on phase change materials," Nature Photonics, vol. 10, 2016, 13 pages.
Xie, R., et al., "Spinodal Dewetting of Thin Polymer Films," Physical Review Letters, vol. 81, No. 6, Aug. 10, 1998, pp. 1251-1254.
Yan, Wei, et al., "Semiconducting Nanowire-based Optoelectronic Fibers," Advanced Materials, vol. 29, 2017, 17 pages.
Yan, Wei, et al., "Advanced Multimaterial Electronic and Optoelectronic Fibers and Textiles," Advanced Materials, vol. 31, 2019, 28 pages.
Yang, Yuanmu, et al., "All-dielectric metasurface analogue of electromagnetically induced transparency," Nature communications, vol. 5, 2014, 7 pages.
Yang, Yuanmu, et al., "Nonlinear Fano-resonant Dielectric Metasurface," Nano Letters, vol. 15, 2015, 18 pages.
Yanik, Ahmet A., et al., "Seeing protein monolayers with naked eye through plasmonic Fano resonances," Proceedings of the National Academy of Sciences, vol. 108, No. 29, Jul. 19, 2011, pp. 11784-11789.
Ye, Jongpil, et al., "Templated Solid-State Dewetting to Controllably Produce Complex Patterns," Advanced Materials, vol. 23, 2011, pp. 1567-1571.
Yesilkoy, Filiz, et al., "Phase-sensitive plasmonic biosensor using a portable and large field-of-view interferometric microarray imager," Light: Science & Applications, vol. 7, 2018, 9 pages.
Yildirim, Adem, et al., "Surface Textured Polymer Fibers for Microfluidics," Advanced Functional Materials, vol. 24, 2014, pp. 4569-4576.
Yu, Nanfang, et al., "Light Propagation with Phase Discontinuities: Generalized Laws of Reflection and Refraction," Science, vol. 334, Oct. 21, 2011, pp. 333-337.
Yu, Nanfang, et al., "Flat optics with designer metasurfaces," Nature Materials, vol. 13, Feb. 2014, pp. 139-150.
Zha, Yunlai, et al., "Solution-processing of thick chalcogenide-chalcogenide and metal-chalcogenide structures by spin-coating and multilayer lamination," Optical Materials Express, vol. 3, No. 2, Feb. 1, 2013, pp. 309-317.
Zhang, Li, et al., "Ultra-thin high-efficiency mid-infrared transmissive Huygens meta-optics," Nature Communications, vol. 9, 2018, 9 pages.
Zheludev, Nikolay I., et al., "From metamaterials to metadevices," Nature Materials, vol. 11, Nov. 2012, pp. 917-924.
Zou, Yi, et al., "Solution Processing and Resist-Free Nanoimprint Fabrication of Thin Film Chalcogenide Glass Devices: Inorganic-Organic Hybrid Photonic Integration," Advanced Optical Materials, vol. 2, 2014, 6 pages.
Zywietz, Urs, et al., "Laser printing of silicon nanoparticles with resonant optical electric and magnetic responses," Nature Communications, vol. 5, 2014, 7 pages.
International Search Report dated Apr. 13, 2017, issued in International Application No. PCT/EP2016/0783741, 6 pages.
Written Opinion of the International Searching Authority dated Apr. 13, 2017, issued in International Application No. PCT/EP2016/078341, 10 pages.

* cited by examiner

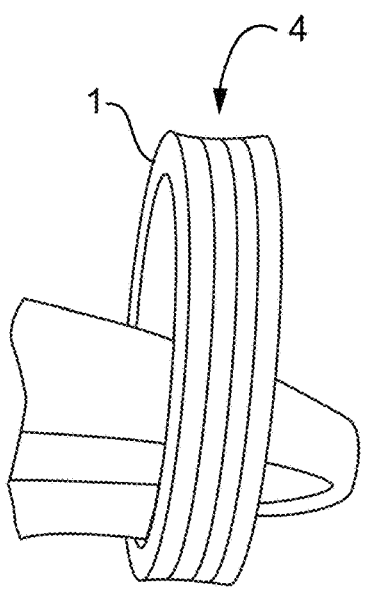
Figure 6
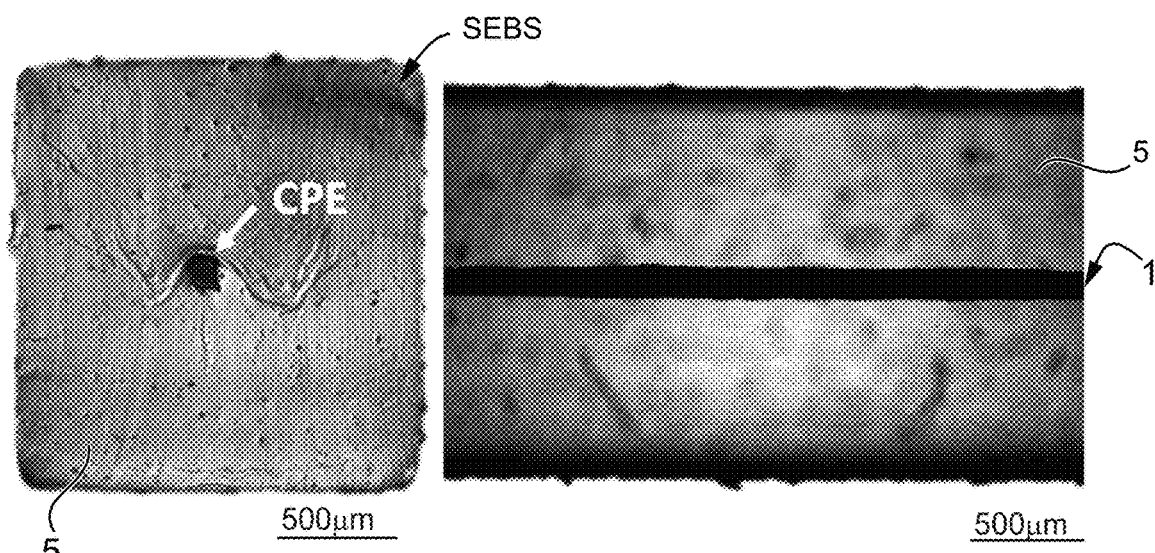
Figure 7A
Figure 7B
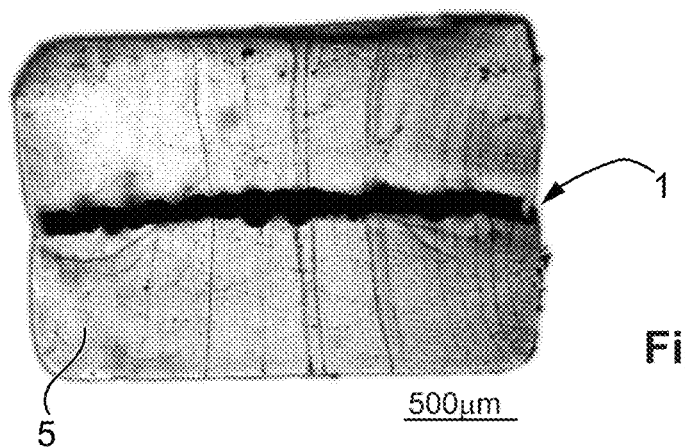
Figure 7C

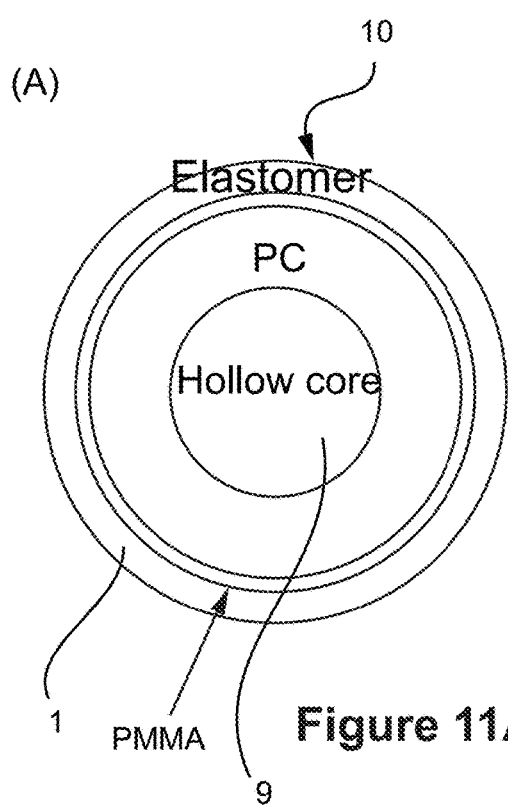
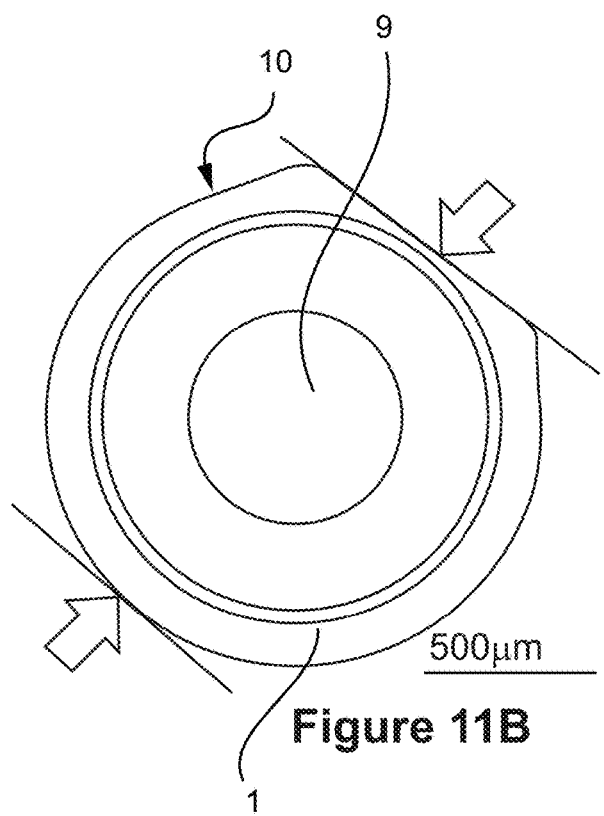
Figure 11A
Figure 11B
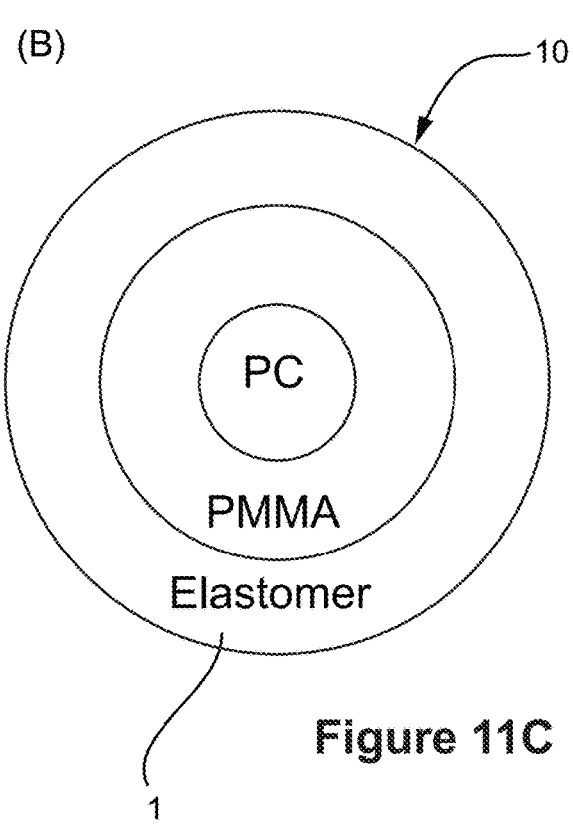
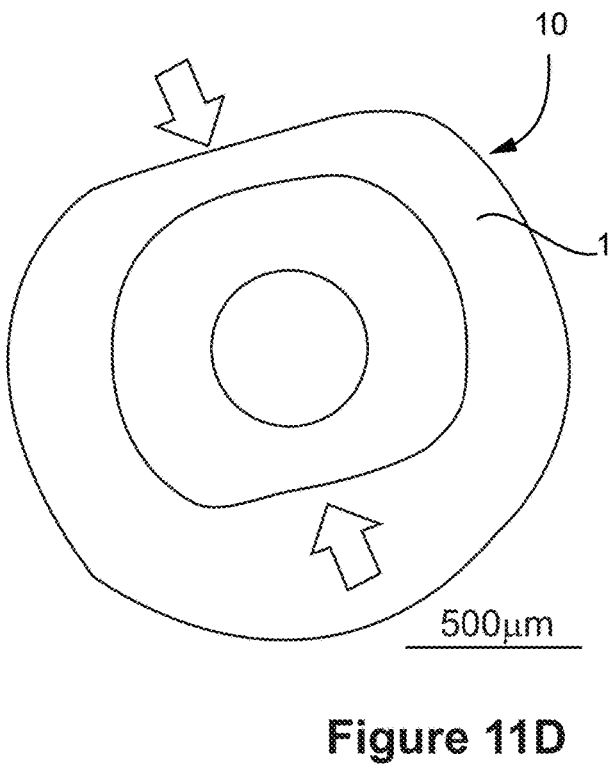
Figure 11C
Figure 11D

MULTI-MATERIAL STRETCHABLE OPTICAL, ELECTRONIC AND OPTOELECTRONIC FIBERS AND RIBBONS COMPOSITES VIA THERMAL DRAWING

CORRESPONDING APPLICATION

The present application is the U.S. national phase of International Application No. PCT/M2017/050749 filed Feb. 10, 2017 which designated the U.S. and claims priority to European application No 16155102.3 filed on Feb. 10, 2016, in the name of ECOLE POLYTECHNIQUE FEDERAL DE LAUSANNE (EPFL), the entire contents of each of which are hereby incorporated by reference.

FIELD AND SUMMARY OF THE INVENTION

The ability to make materials and devices with for example optical, electronic or optoelectronic functionalities that can be robust upon stretching, bending, torsion or other mechanical deformation constitutes a relatively recent yet extremely active research thrust. Reliable, low losses and stretchable electrical interconnect and optical fibers or waveguides, can bring significant advancements in the field of electrical and optical cables, in prosthesis, robotics, smart or medical textiles, or wearable electronics and photonics and other related fields.

Energy harvesting from mechanical movement or various radiation, stretchable displays, pressure sensors or devices capable of interfacing with biological tissues are other fields where the development of stretchable devices will constitute a key breakthrough.

The main challenges associated with the fabrication of stretchable systems are two folds:
(1) to reconcile the optical or electronic materials that are traditionally rigid with the compliance with harsh mechanical constraints; and
(2) to process in a simple and scalable way such systems with micro and/or nano-structures.

In the present invention, both challenges are tackled by applying, for the first time, a thermal drawing process to stretchable materials such as thermoplastic elastomers. Traditionally, this process is associated with rigid, high modulus silica or thermoplastic polymers, with a glass transition temperature well above room temperature.

In the present invention, it is demonstrated that some elastomeric materials can in fact be processed with this technique at high viscosity, enabling to make fibers with any cross-sectional shape at the scalability and cost of optical fibers.

Moreover, a variety of materials such as polymers and polymer composites, metals, or semiconductors, among others, can be co-drawn with the stretchable materials. This enables novel device architectures for stretchable electronic and photonic. For example, electrical interconnects integrating liquid-metal wires with arbitrary size and number of wires can be fabricated, that can maintain a high level of conductivity even upon stretching up to 400%. In a further effect, they can sense deformation. Stretchable optical fibers and waveguides can also be fabricated, as well as photonic bandgap structures that can change color upon mechanical stress.

As a result, this opens a new class of fiber devices in fields of smart textiles, bioengineering, health care, energy harvesting and sensors.

BACKGROUND OF THE INVENTION

Thermal drawing technique is the main technique that is used to fabricate optical fibers, see reference [1]. In the drawing process of the prior art, a large preform made of glass or polymer that are rigid at room temperature, is fed into an enclosed furnace and heated over its glass transition temperature. As the viscosity decreases several orders of magnitude, the preform necks down under its own weight; when the lower end of the preform comes out of the furnace, it is attached to a pulling system, and the fiber is then continuously drawn. Fiber dimension, shape and internal stress are monitored during the process by optical sensor and tension sensor; and they are controlled by a set of drawing parameters, namely feeding speed (the speed at which the preform is fed into the furnace), drawing speed (the speed at which the fiber is pulled) and the furnace temperature. The principle of this technology is illustrated in FIG. 1.

Since the invention of low-loss optical fiber by Charles Kao see reference [1], which redefined the way of communication, the thermal drawing process has been a subject for intensive research and has become extremely efficient in term of scaling-down ratio and ease of processing. New generations of fibers have emerged, such as photonic crystal fibers see reference [2] or multimaterial fibers see reference [3], bringing thermally drawn fibers to a wide range of application from optics and electronics to microfluidics and bioengineering.

However so far, this approach has never been applied to stretchable polymers. All fibers and ribbons realized so far had a cladding material, or any of its constituents, made out of nonelastic or nonrubbery materials at room temperature. This is because of a common belief that can be found in many reviews on fiber thermal drawing, see references [3-6], that only glassy homogeneous materials could be drawn in the conventional condition of relatively high viscosity. In the art there exists a technical prejudice to apply a thermal drawing process to stretchable polymers, particularly co-drawn with other functional materials, and other similar materials with similar properties.

The present invention demonstrates that the prior art common belief and thinking is in fact too restrictive and not correct and that materials that are elastic (at room temperature) with a transition temperature above which the viscosity changes gradually (with a higher loss modulus compared to the elastic modulus as shown in FIG. 16) can be thermally drawn.

In particular, certain thermoplastic elastomers that have thermoplastic domain that physically cross-link an elastomeric phase as shown in FIG. 2, can be pulled into long and thin fibers of arbitrary shape.

The present invention also show that these materials can be co-drawn with rheological properties on par with the ones of conventional thermoplastic commonly used for fiber drawing. As shown in FIG. 16, for example, there is a temperature range around which the storage and loss modulus cross over. The loss modulus dominates with a small change with respect to temperature, enabling a controlled drawing experiment similar to the conditions experienced with conventional thermoplastics. They can hence maintain complex device structures during drawing, with multi-material architectures. This leads to novel stretchable device structures and functionalities not realized so far, at the scalability and cost of optical fibers.

OVERVIEW OF THE INVENTION

An aim of the present invention is therefore to improve the known processes and methods, expand the range of materials compatible with said methods and processes, and the products that may be obtained by said processes and methods.

Another aim is to generate novel stretchable fiber, ribbon, or with any cross-sectional shape, based devices with innovative materials and architectures to perform unforeseen functionalities. For example, thermally drawn stretchable fibers with an array of liquid metallic microwires for stretchable electronic interconnects.

A further aim of the proposed invention is hence to generate stretchable fibers and ribbons with, but not restricted to, electrical, optical or optoelectronic functionalities and other similar functionalities which are detailed herein as non-limiting examples and embodiments.

Compared to a conventional thermal drawing process of an optical fiber (e.g. described in the U.S. Pat. No. 3,659,915 A see reference [6]) the present invention described herein is differentiated at least by the novel and inventive following modifications, features and technical aspects:

1. A main cladding material that can be thermally drawn, and made out of a stretchable polymer, in particular of a thermoplastic elastomer.
2. A main cladding material that can be thermally drawn, and made out of a stretchable polymer containing nanocomposites. Fillers could be nanoparticles, nanotubes or other nanoscale objects that bring functionality to the polymer and do not prevent thermal drawing.
3. A thermoplastic elastomer cladding that is thermally drawn and can contain metallic electrodes in a liquid or solid state.
4. A thermoplastic elastomer cladding that is thermally drawn and can contain semiconducting materials or other types of functional materials.
5. A thermoplastic elastomer cladding that is thermally drawn and can contain optically transparent polymers forming nanostructured photonic bandgap structures or step-index like configurations to manage light in different ways (guiding, reflection at certain bandwidths . . . )
6. A multi-material fibers that integrate semiconductors, metals, polymer composite and a thermoplastic elastomer that insures stretchability or/and deformability.
7. A stretchable electrical interconnect fabricated by the thermal drawing process with metal electrodes (Ga, Galinstan . . . ) inside a thermoplastic cladding.
8. A stretchable multi-material fibers that can have metal electrodes exposed at its surface and not necessary fully embedded inside the polymer matrix.
9. A stretchable multi-material fiber that can sense strain or pressure electrically via a change of resistance of embedded conducting material upon stretching or pressing of the fiber;
10. A stretchable multi-material fiber that can sense strain or pressure optically via a change of light transmission upon stretching or pressing of the fiber;
11. A microstructured fiber that can deform upon pressure and/or stretching, via an electrical signal (resistivity or capacitance) that depends on the direction of the excitation (compression, stretch, shear, torsion etc. . . . ).
12. A deformable and/or stretchable fiber that can generate power via a triboelectric configuration. The fiber integrate a multi-material architecture where different rigid or soft polymers are separated by a gap. When pressure or stretch is applied, the polymers get into contact, generating a triboelectric effect resulting in a voltage drop.
13. A stretchable optical fiber in which the light is propagating within rigid high transparency thermoplastic polymers, in step-index or other light guiding configurations;
14. Textured stretchable fibers and/or ribbons with the texture being created at the preform level via hot embossing, casting, or other texturing techniques as disclosed in the application PCT/EP2016/078341 entitled NOVEL FABRICATION METHOD OF FUNCTIONAL MICRO/NANO STRUCTURES OVER LARGE-AREA, FLEXIBLE AND HIGH CURVATURE SURFACES.
15. A rigid polymer fiber embedded inside a stretchable cladding. This fiber can be stretched and recover its initial length by imposing a non straight structure (wavy.) to the rigid inner core
16. A rigid polymer fiber embedded inside a stretchable cladding. This fiber can be rigid in the axis direction to penetrate a brain tissue for example, but soft in the transverse direction to comply with the tissue mechanical properties.

Accordingly, in an embodiment the invention concerns a thermal drawing method for forming at least a fiber, wherein said method comprises the steps of providing a preform of a material heating said material such that the preform necks down under its own weight and produces a lower end, continuously drawing a fiber from said lower end of the preform, wherein said material comprises at least a stretchable polymer.

In an embodiment the stretchable polymer is a thermoplastic elastomer.

In an embodiment the fiber is co-drawn with at least another material.

In an embodiment the fiber contains at least a metallic electrode made of a conductive medium. The conductive medium may be liquid or solid or in another form.

In an embodiment of the method, to interface electrically with the embedded electrode of the fiber, a thin metallic wire(s) is inserted in the channel containing the electrode, and epoxy or other glue type system are used to encapsulate and ensure a good mechanical resistance of the connection.

In an embodiment the material of the preform may comprise nanoscale objects to bring functionality to the material. The nanoscale objects may comprise nanoparticles and/or nanotubes or other equivalent materials.

In an embodiment, the invention concerns a drawn fiber formed by a method as defined in the present specification.

In an embodiment the fiber is drawn from a heated preform of a material, and the material used for the fiber comprises at least a stretchable polymer.

The polymer may be a thermoplastic elastomer.

In an embodiment the material may contain nanoscale objects to bring functionality to the material. The nanoscale objects may be nanoparticles and/or nanotubes or other equivalents.

In an embodiment the fiber forms a thermoplastic elastomer cladding that is thermally drawn and contains metallic electrodes.

In an embodiment the electrode is in a liquid or solid state. For example, the electrode may be made of Gallium or Galinstan.

In an embodiment the fiber may contain semiconducting materials or other types of functional materials.

In an embodiment the fiber may contain optically transparent polymers forming photonic bandgap structures or step-index like configurations to manage light (for guiding, reflection purposes and other etc. . . . ).

In an embodiment the fiber may form a multi-material structure that integrate semiconductors, metals, polymer composite and a thermoplastic elastomer that insures stretchability or/and deformability.

In an embodiment the fiber may sense elongation, or pressure via the change of electrical current or optical transport properties of embedded functional materials and structures of the fiber as described herein.

In an embodiment the fiber may contains a variety of pair of polymers such as PMMA-SEBS, PEI-PC or other suitable materials, or nanocomposites separated by a gap to generate charges as they are brought in contact In an embodiment the fiber may comprise embedded electrodes that enables to collect a voltage and generate power upon mechanical deformation of the fiber.

In an embodiment the fiber may comprise metal electrodes or other conducting materials exposed at its surface.

In an embodiment of the fiber, light may propagate within rigid high transparency thermoplastic polymers of the fiber.

In an embodiment the fiber may comprise ribbons forming a texture at the preform level via hot embossing, casting, or other texturing techniques;

In an embodiment the fiber is embedded inside a stretchable cladding, wherein said fiber can be stretched and recover its initial length by imposing a non straight structure to a rigid inner core.

In an embodiment the fiber is embedded inside a stretchable cladding, wherein said fiber is rigid in the axis direction to penetrate a tissue, and/or soft in the transverse direction to comply with the tissue mechanical properties.

DETAILED DESCRIPTION OF THE INVENTION

The present invention will be better understood from the following description of non-limiting examples and embodiments, some illustrated in the attached drawings which show FIG. 1 represents a bloc-diagram of an example of a thermal drawing process from a preform according to the prior art;

FIGS. 2A to 2F illustrate an example of poly(styrene-block-butadiene-block-styrene) (SEBS) preform 2 and SEBS fiber 1 after thermal drawing, FIGS. 2A and 2B. It also shows a schematic illustration of a thermoplastic elastomer, FIG. 2C. A Transmission Electron Microscope (TEM) micrograph shows the microstructure of the preform (FIG. 2D) and the drawn polymer (FIGS. 2E and 2F). The structures are similar highlighting the fact that the thermal drawing process does not alter the elastic properties of the polymer.

FIGS. 3A and 3B illustrate an example of a fiber 1 made of a copolymer of polydimethylsiloxane and urea (Geniomer) preform 2.

FIGS. 4A to 4F illustrate an example of SEBS fiber 1 with liquid Gallium 3 inside. FIGS. 4A and 4B show the side view and cross-section view respectively of a SEBS fiber integrating 8 liquid Ga electrodes. In FIG. 4C, the preform 2 is schematically shown with the fiber 1 being drawn according to the present invention (FIG. 4D). FIG. 4E shows the cross-section and longitudinal view of a single Ga electrode embedded in the SEBS cladding. The picture below shows that the electrode is continuous over tens of meters, and can be used to light an LED. The fiber 1 obtained can act as a strain sensor since the electrical current through the wire depends on the fiber strain as shown in the graph, see FIG. 4F. This makes a very robust and stable sensor, as an example of application.

FIG. 6 represents a fiber 1 with a stretchable polymer matrix and exposed metallic electrodes 4 on the fiber surface, in contrast with the embedded electrodes previously shown.

FIGS. 7A to 7B illustrate an example of SEBS fiber 1 with a polymer nanocomposite with Carbon black loaded polyethylene (CPE) inside. In the bottom (FIG. 7C) is a SEBS-Carbon Nanotube composite (in black) thermally drawn within a SEBS matrix 5.

Figure 8A:
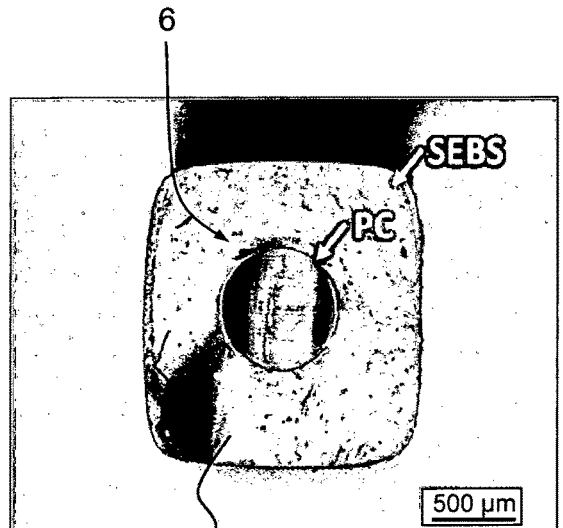
Figure 8B:
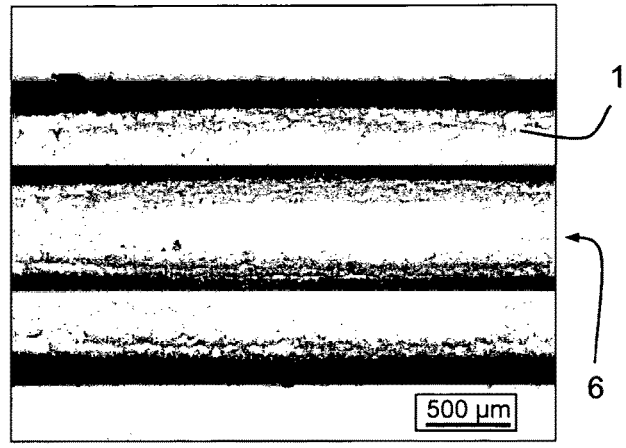
Figure 8C:
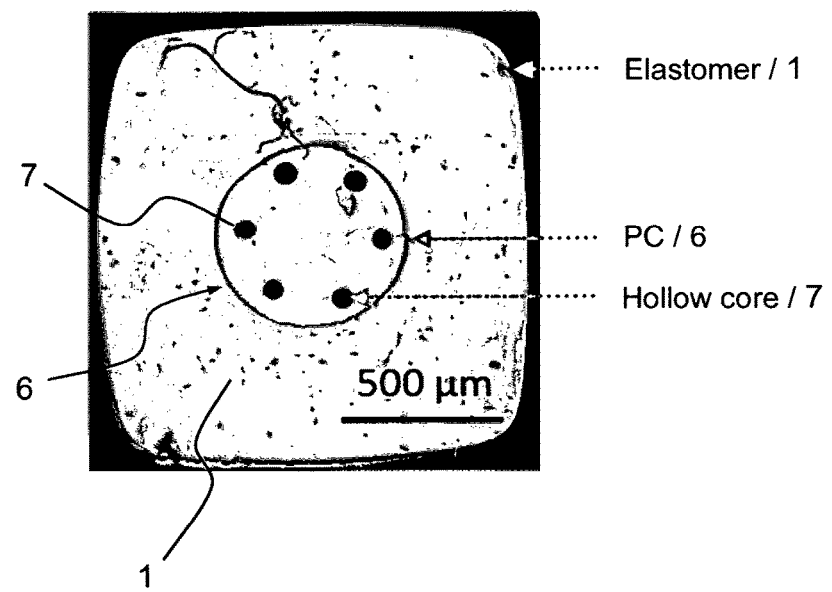
Figures 9A, 9B:
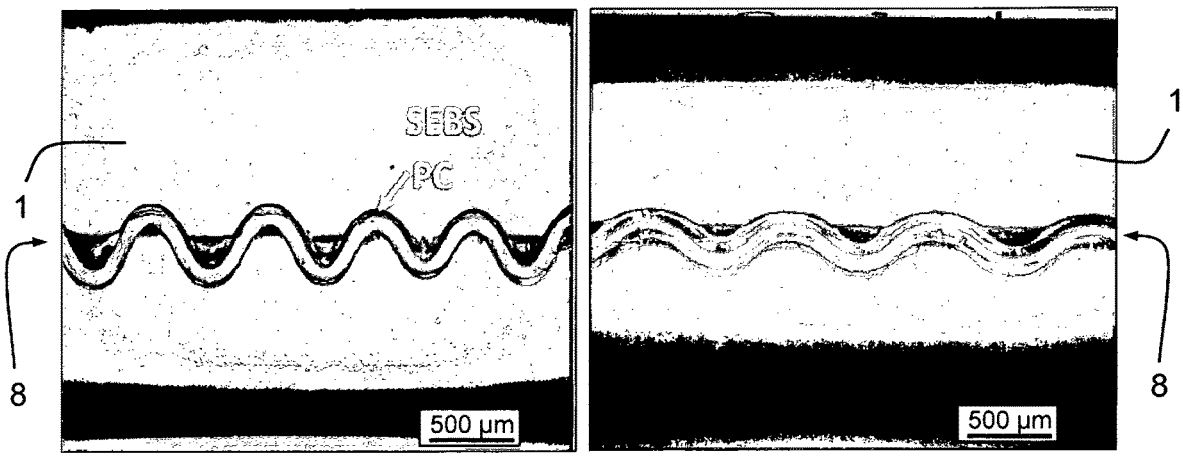
Figure 9C:
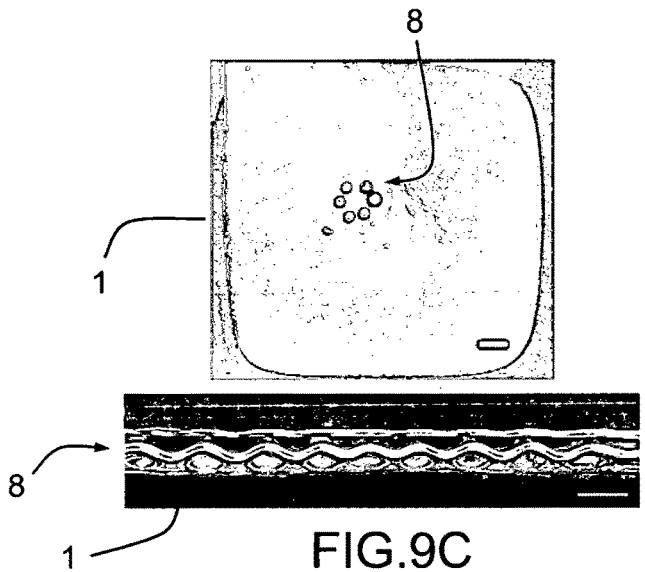
Figure 9D:
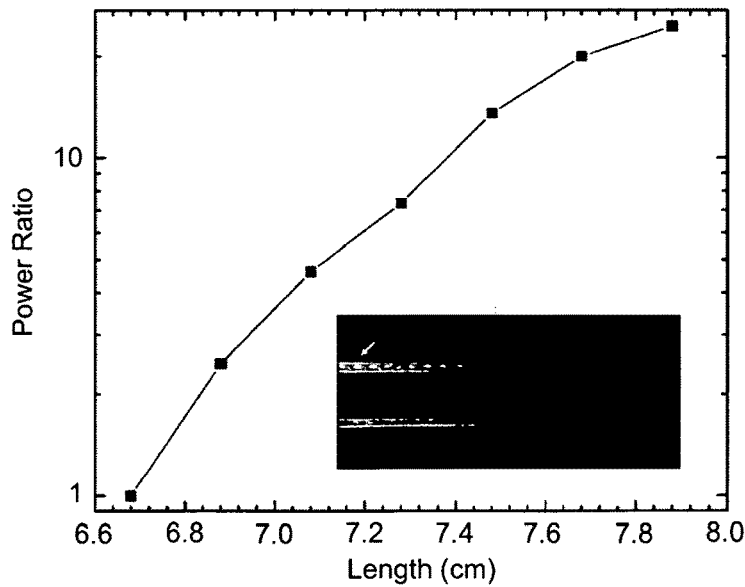

FIGS. 8A to 8C illustrate an example of SEBS fiber 1 with Polycarbonate (PC) thermoplastic 6 inside. FIG. 8C is an example of a microstructured PC fiber with hollow channels 7, within a stretchable cladding.

FIGS. 9A to 9D illustrate an example of SEBS fiber 1 with wavy PC 8 rod inside. In the bottom left (FIG. 9C), the fiber 1 of FIGS. 8A-8C was strained, inducing the microstructured PC 8 to deform plastically. As the stress is released the PC 8 deforms into a helicoidal shape to comply with the initial length recovered by the elastic cladding 1. Launching light as shown in bottom right FIG. 9D creates a strain dependent loss optical fiber 1. At each bend, light can escape but as the fiber 1 is stretched, the bend radius reduces and less light couples out, leading to lower losses.

Figure 10A:
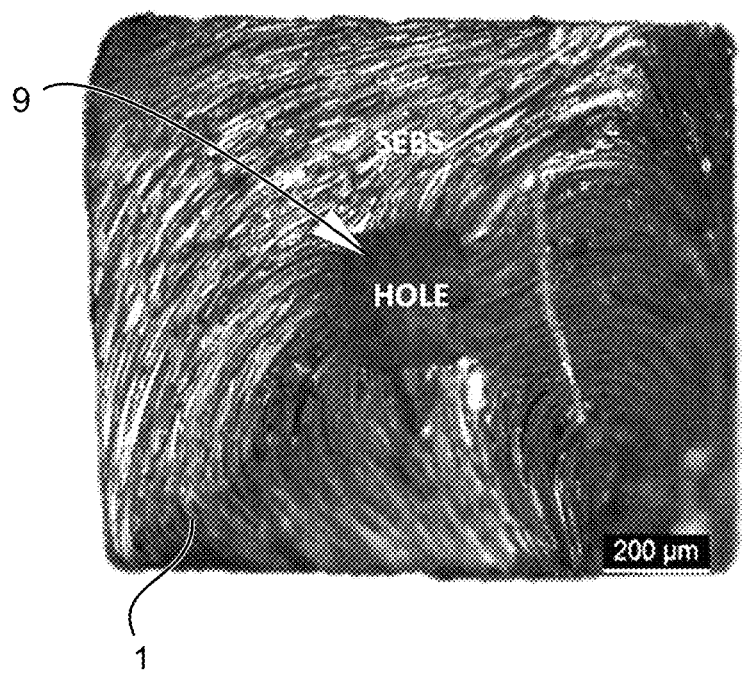
Figure 10B:
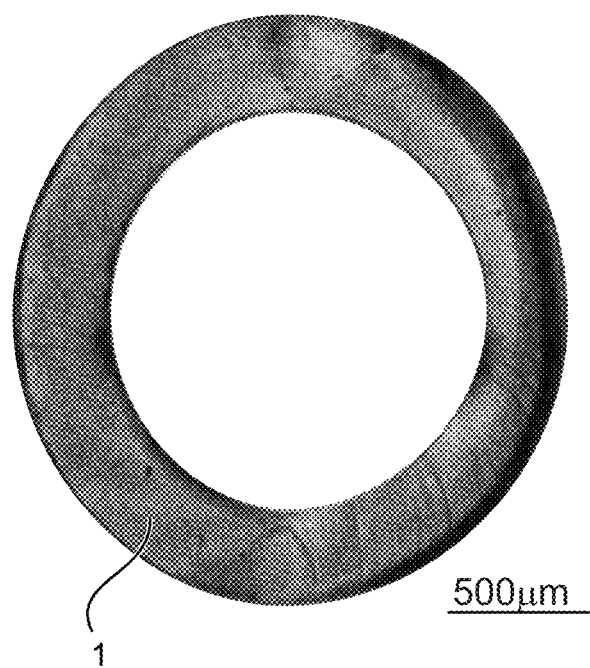

FIGS. 10A and 10B illustrate two examples of SEBS fiber 1, a rectangular and circular shaped, with a hollow channel 9 inside.

FIGS. 11A to 11D illustrate two examples of optical fibers 1 with a soft cladding 10. These fibers can be rigid in the z direction, but soft along their side for, for example, avoid tissue irritation for fiber probes. One fiber has a hollow channel 9.

Figure 12A:
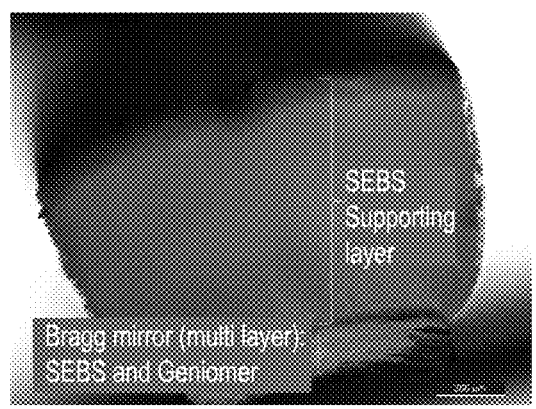
Figure 12B:
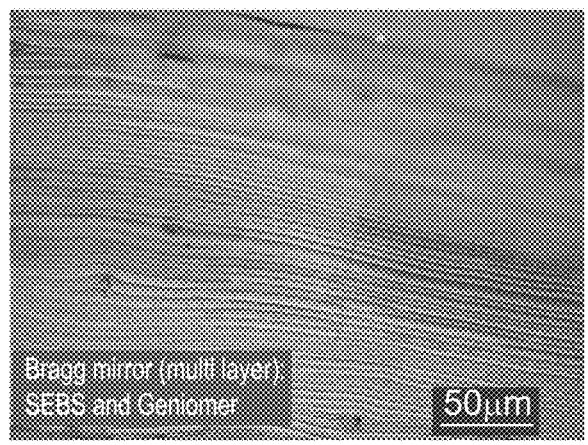
Figure 12C:
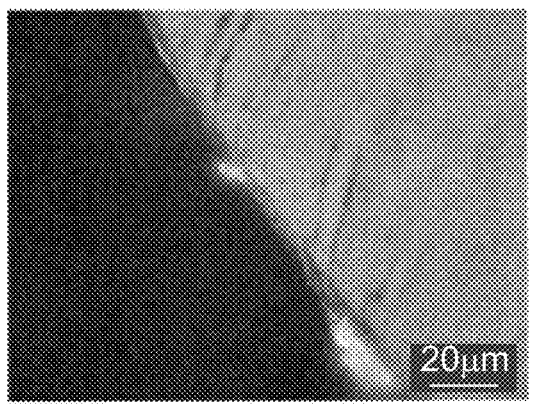

FIGS. 12A to 12C illustrate examples of multilayer Bragg mirror fiber 1, a stack of alternative layers made of SEBS and Geniomer. FIG. 12C shows a similar bragg mirror fabricated around a circular SEBS fiber.

Figure 13:
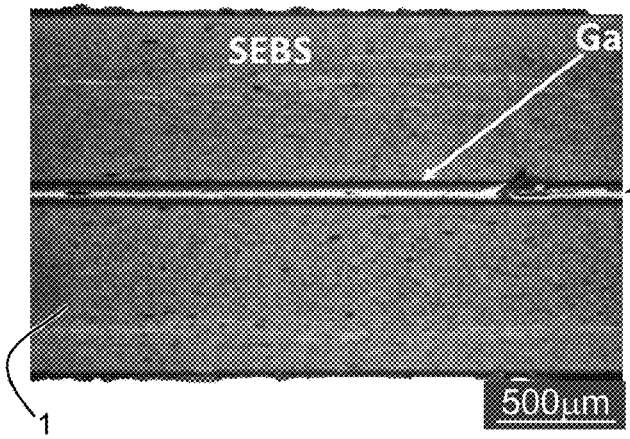

FIG. 13 illustrates examples of liquid Gallium 11 in the channel in SEBS fiber 1 surface.

Figures 14A, 14B, 14C:
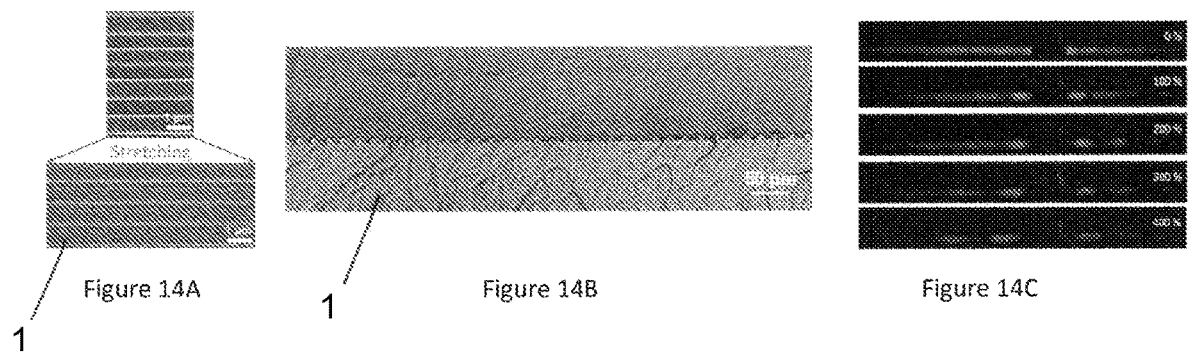

FIGS. 14A to 14C shows SEM (top view, FIG. 14B) and optical microscope (cross-section, FIG. 14A) pictures of a textured fiber 1 made out of a stretchable polymer. On the right (FIG. 14C), a diffraction pattern is shown to shift as the fiber is being stretched.

Figure 15A:
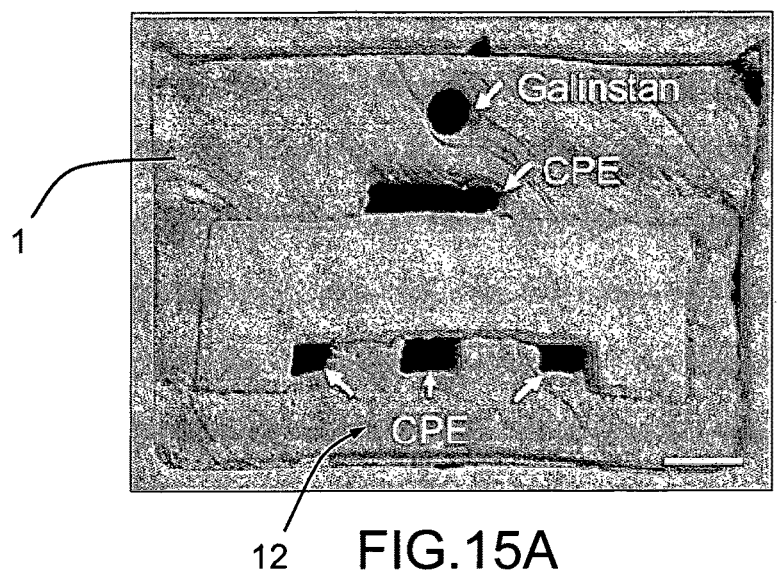
Figure 15B:
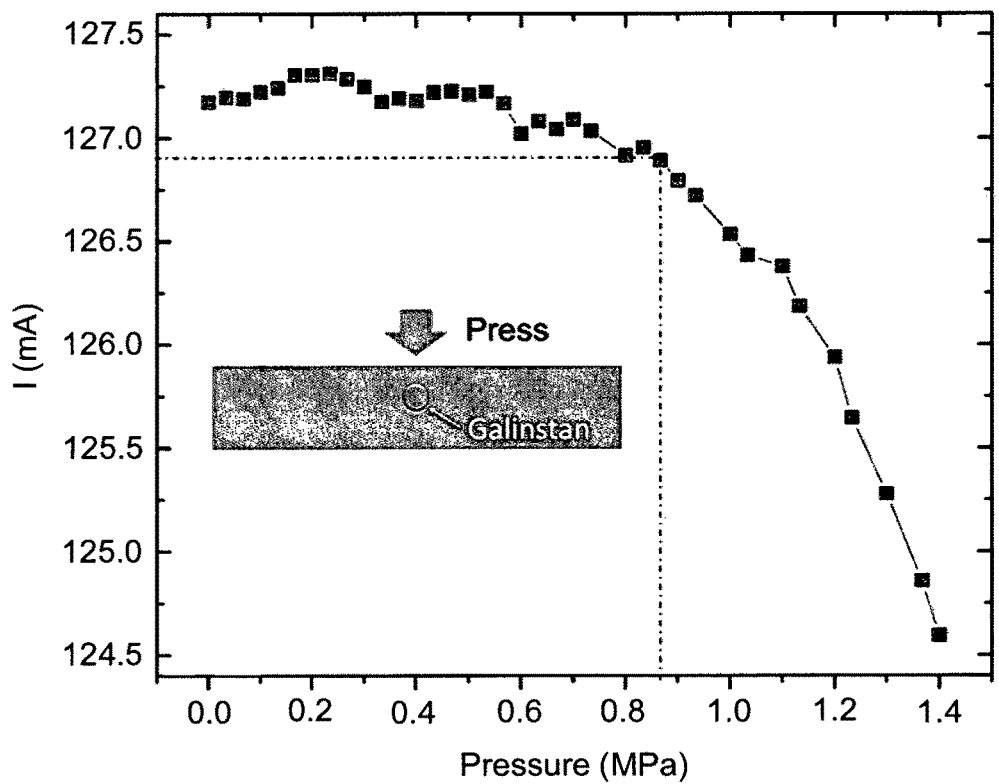

FIGS. 15A and 15B show the optical micrograph of a stretchable multi-material fiber 1 with a complex architecture that can sense pressure and its direction. Depending on the direction for the pressure, the top CPE electrode can touch a different CPE electrode in the bottom connected to different circuits, hence revealing the pressure direction. A metallic layer 12 right under the surface can sense pressure as shown in the graph where a change of current is shown as a pressure is applied.

Figure 16:
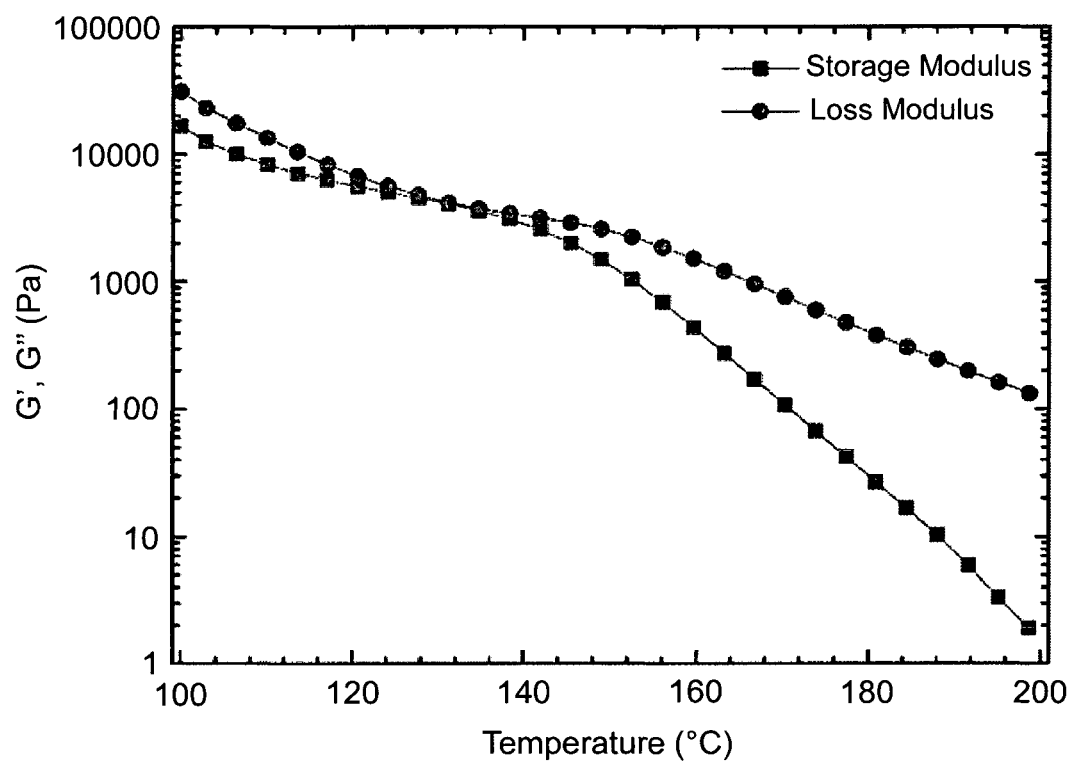

FIG. 16 shows the storage (G') and loss modulus (G") of SEBS, highlighting a new criteria used to evaluate compatibility with the drawing process by requiring a situation where G">G', so that a cross over between the two must happen in some temperature range.

Figure 17A:
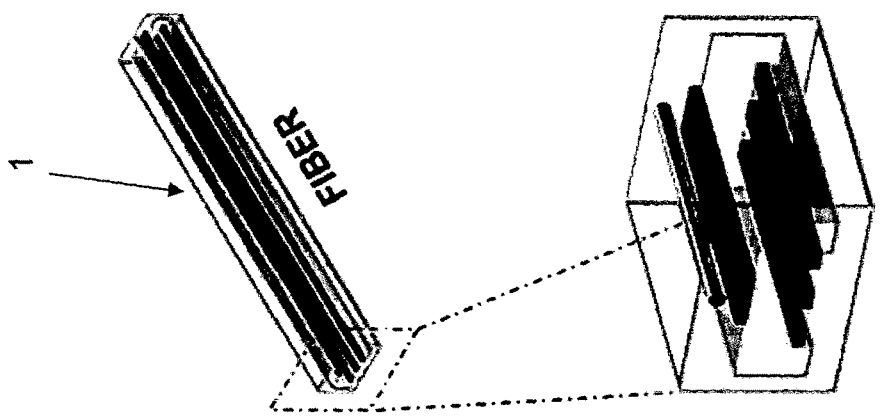
Figure 17B:
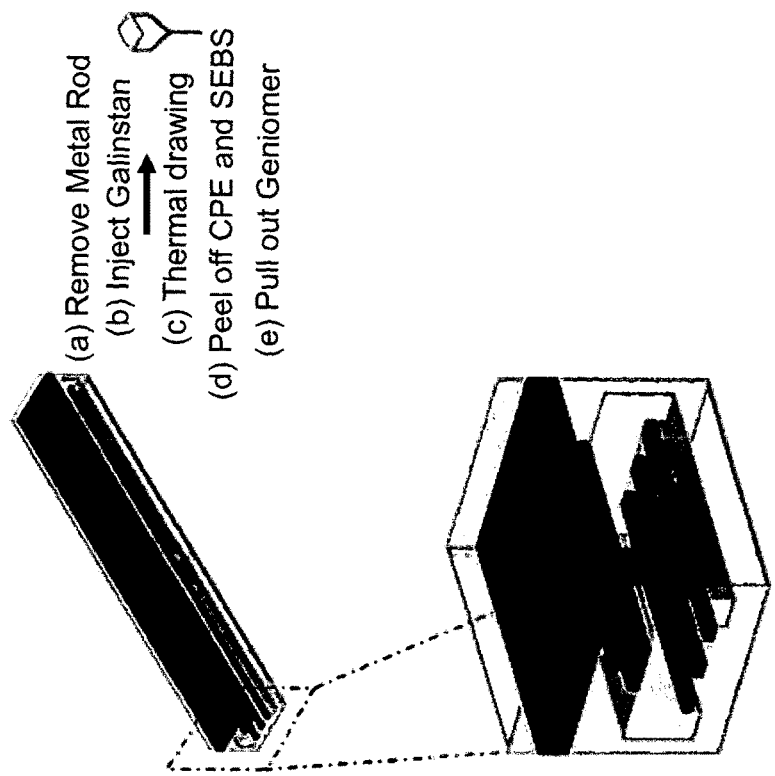

FIG. 17 illustrates an example of a touch sensing fiber and the processing steps to fabricate the same. The preform is fabricated layer by layer as illustrated in FIGS. 17A and 17B and in the steps (a) to (e) listed in FIG. 17B and the whole assembly is then thermally drawn to form the fiber in accordance with the principles of the present invention.

DETAILED DESCRIPTION

Thermal plastic elastomer (TPE) is a kind of copolymers or of physically mixed polymers (usually a plastic and a rubber) which comprises materials with both thermoplastic and elastomeric properties. For example, poly(styrene-block-butadiene-block-styrene or SEBS) is a very typical kind of TPE. The glass transition (Tg) of the polystyrene (PS) part is ca. 120° C., higher than room temperature (RT), so it serves as a thermoplastic part at RT. The Tg of poly(butadiene-block-styrene) (EB block) is –50 to –60° C., lower than RT and hence it forms an elastic part. At RT, the PS will provide a physical cross link (i.e. aggregate), that will ensure that the elastomer will return to its original shape when the stress is removed. When the TPE is heated above the Tg of PS, the physically crosslinked thermoplastic part is "uncrosslinked", which enable deformation and thermal drawing.

The main difference between TPEs and thermal set rubbers is that thermoset rubbers are chemically cross linked with covalent bonds between the chains. These bonds cannot be destroyed before thermal degradation, so thermal set rubbers cannot be remanufactured, and could not be thermally drawn. The physically cross linked PS domains in the preform are distributed in the ES block matrix and prevent the further slip of EB block after the EB block reaches its maximum stretch ratio under a mechanical constraint. For SEBS to be compatible with the thermal drawing process, the PS domain must be able to deform or be broken down into smaller parts above the $T_g$ of PS. In a large temperature range SEBS is hence compatible to be codrawn with many different kinds of materials, such as high-drawn-temperature polycarbonate (PC), low-drawn temperature poly(lactic-co-glycolic acid) (PLGA), and different metals or semiconductors with various melting points.

The microstructure of TPE in the final fiber and thus the mechanical property is highly temperature dependent. At lower drawing temperatures, for example, 140° C., PS block will maintain a strong phase separation with EB block (similar to the preform state), while PS domain is able to be deformed and drawn. In such low temperature, the PS domain is large and will be reoriented along the thermal drawing direction as demonstrated in the small-angle X-ray scattering (SAXS) and transmission electron microscopy (TEM) results. In the case of high drawing temperature, such as 220° C., the PS block tend to form small domains, and do not aggregate as much. Thus the PS domain in the low-drawing-temperature fiber is larger than for the high-drawing temperature, in the drawing direction. The larger PS domain size could bring a higher modulus as could be found in the strain-stress test.

To make a TPE drawable, the TPE should have the following properties:
1. Good thermal resistance. The polymer should not thermally degrade during the drawing process. The thermal resistance property of the elastic block is the key point as commonly the elastic block will degrade thermally before the plastic one due to its lower Tg. One of the good candidate of TPE is SEBS as its EB block is hydrogenated to get rid of the double bond and its thermal degradation temperature could be as high as ca. 280° C. This is high enough to cover a large part of materials for the multimaterial fiber drawing.
2. Proper viscosity and (melt) strength to be compatible with the drawing process and other co-drawn materials. This could be one main challenge in finding a proper TPE to be drawn as interchain interaction between the elastic block is rather week, especially at high temperature, due to the low Tg. The intrachain interaction and the plastic component domain are two aspects we could think about to improve. A high molecular weight, i.e., long polymer chain will increase the polymer entanglement and thus is good for increasing the viscosity and strength.
3. The plastic component domain property (such as molecular weight and its ratio to the elastic block) is another important part to determine the viscosity and strength which is highly dependent on temperature in terms of phase separation and plastic domain size. It should be properly tailored when making the preform and drawing a fiber. A low drawing temperature will be important to maintain a high viscosity and (melt) strength.
4. The TPE, especially the plastic part, should resist crystallization as crystal melt could bring a sudden drop in viscosity during the thermal process.

EXAMPLES

1. Making SEBS Preform or Plate

A typical process to make a SEBS preform 2, for example, a preform having dimensions 24 mm in width, 170 mm in length and 10 mm in thickness, is the following. The SEBS granule can be acquired from different companies, for example G1657, a product of Kraton Performance Polymers Inc. Its weight-average molecular weight is ca. 70 000 g/mol and the soft/hard ratio is 87/13 (weight). The granule are preferably hot pressed under a pressure of 0.25 bar for 15 min at a temperature at 180° C. The hot press temperature could be varied from 130° C. to 190° C.

2. Thermal Drawing of a SEBS Based Preform.

The preform 2 was put in a furnace. In a typical process, (1) the temperature could be 90° C. in the top zone, 130° C. to 260° C. in the middle zone temperature, and 80° C. in the bottom zone; (2) The drawing speed could be from 0.05 m/min to 2.4 m/min or higher and the feeding speed could be 1 mm/min, for example. Other temperature ranges depending on the materials, and higher drawing speed can be achieved as well. This is illustrated in FIGS. 2A to 2F, which disclose a SEBS fiber 1 after thermal drawing in FIGS. 2A and 2B.

Figure 1:
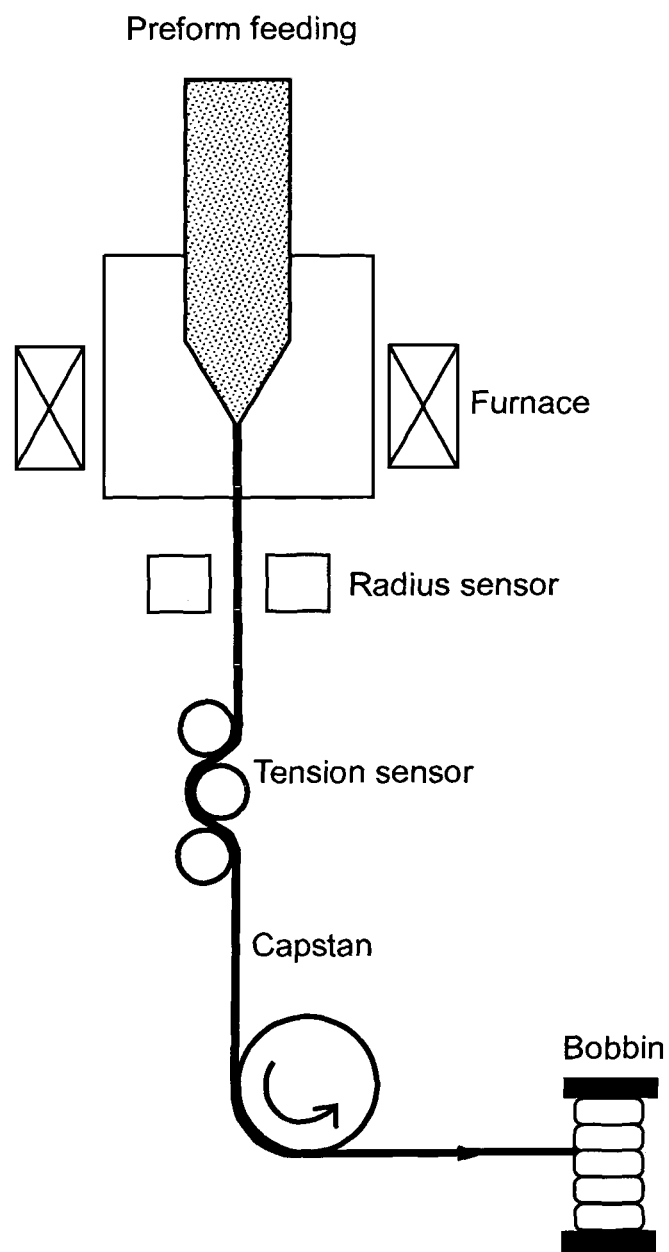
Figure 2A:
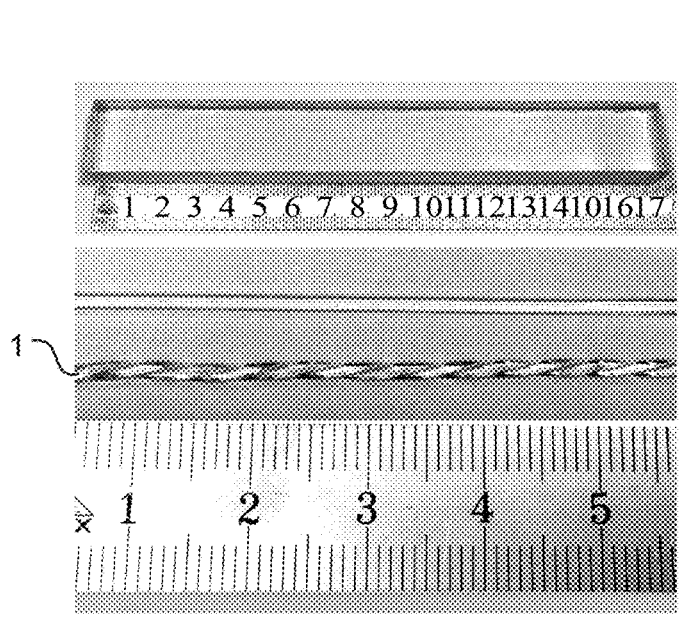
Figure 2B:
Figure 2C:
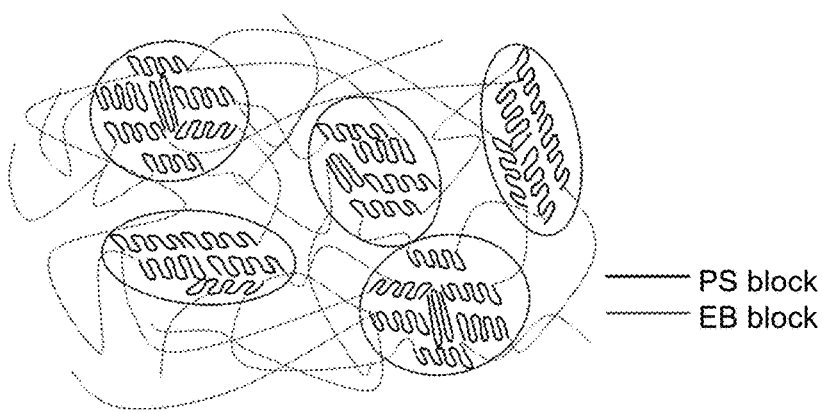

FIG. 2C illustrates schematically a thermoplastic elastomer.

Figure 2D:
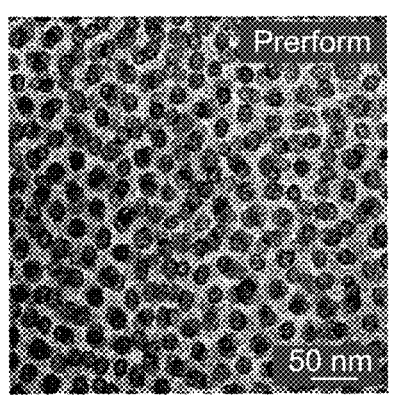
Figure 2E:
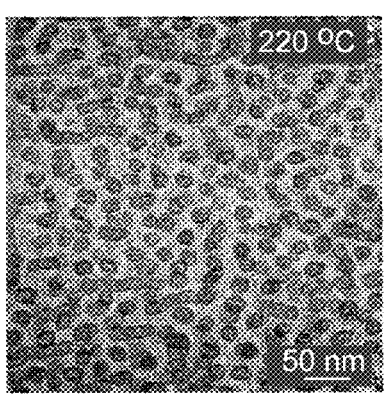
Figure 2F:
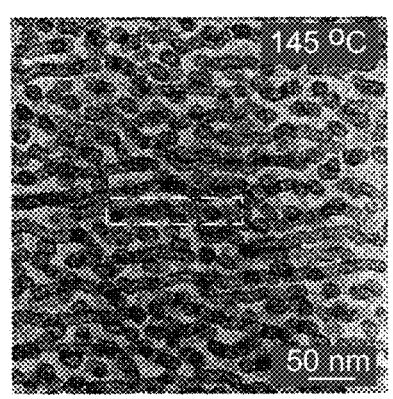
Figures 3A, 3B:
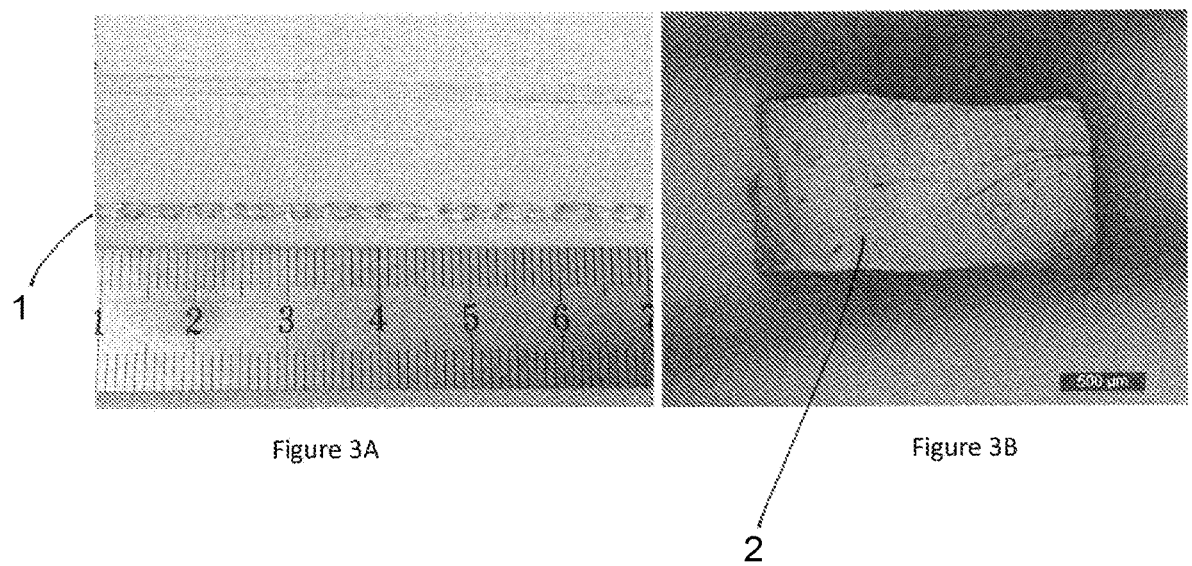
Figure 4A:
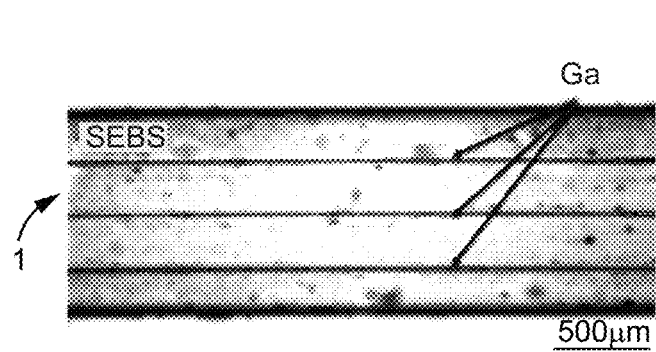
Figure 4B:
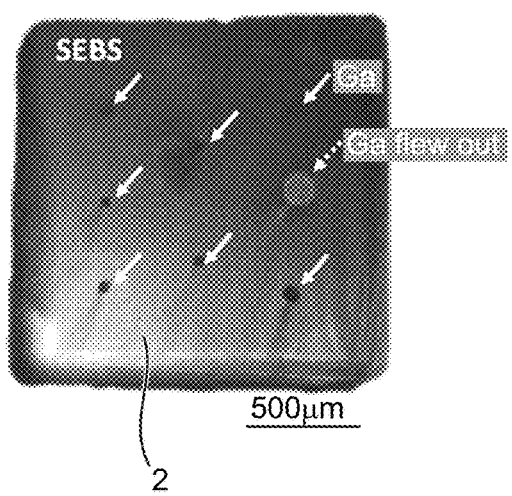
Figure 4C:
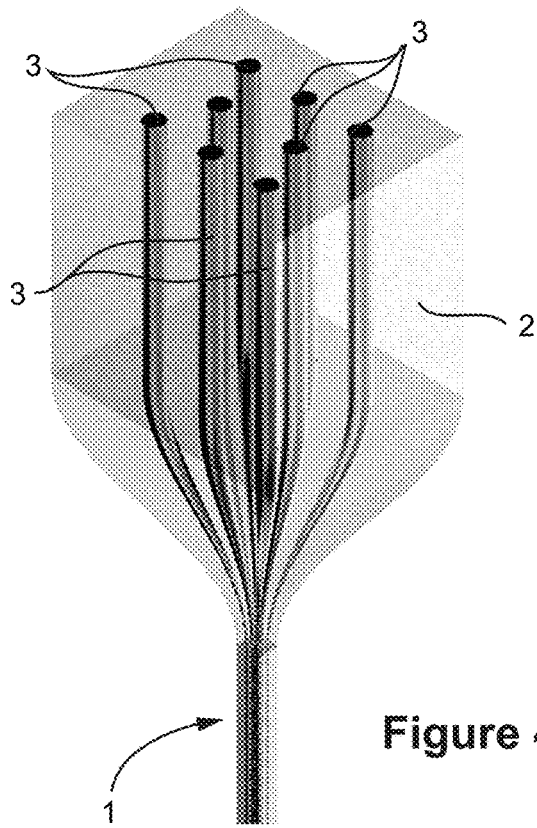
Figure 4D:
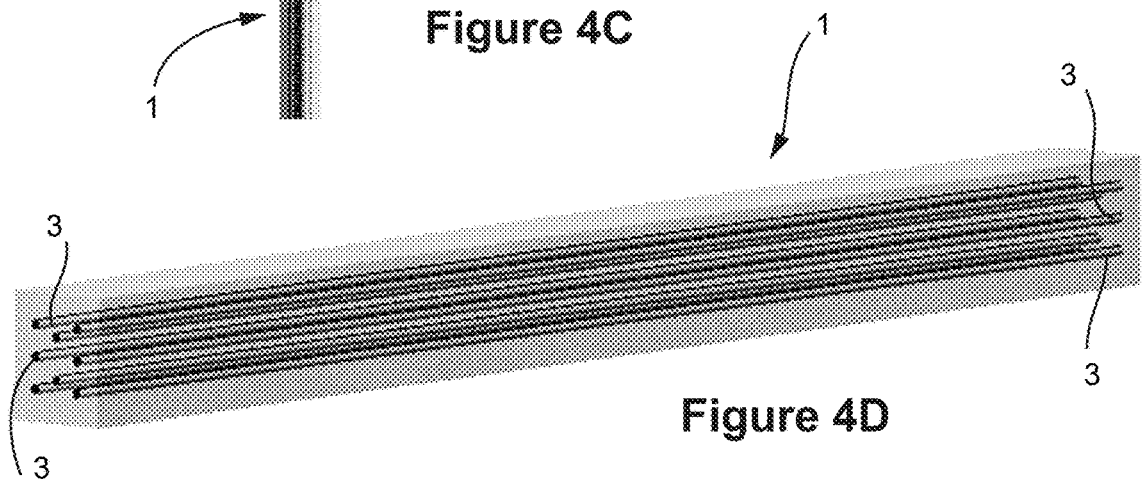
Figure 4E:
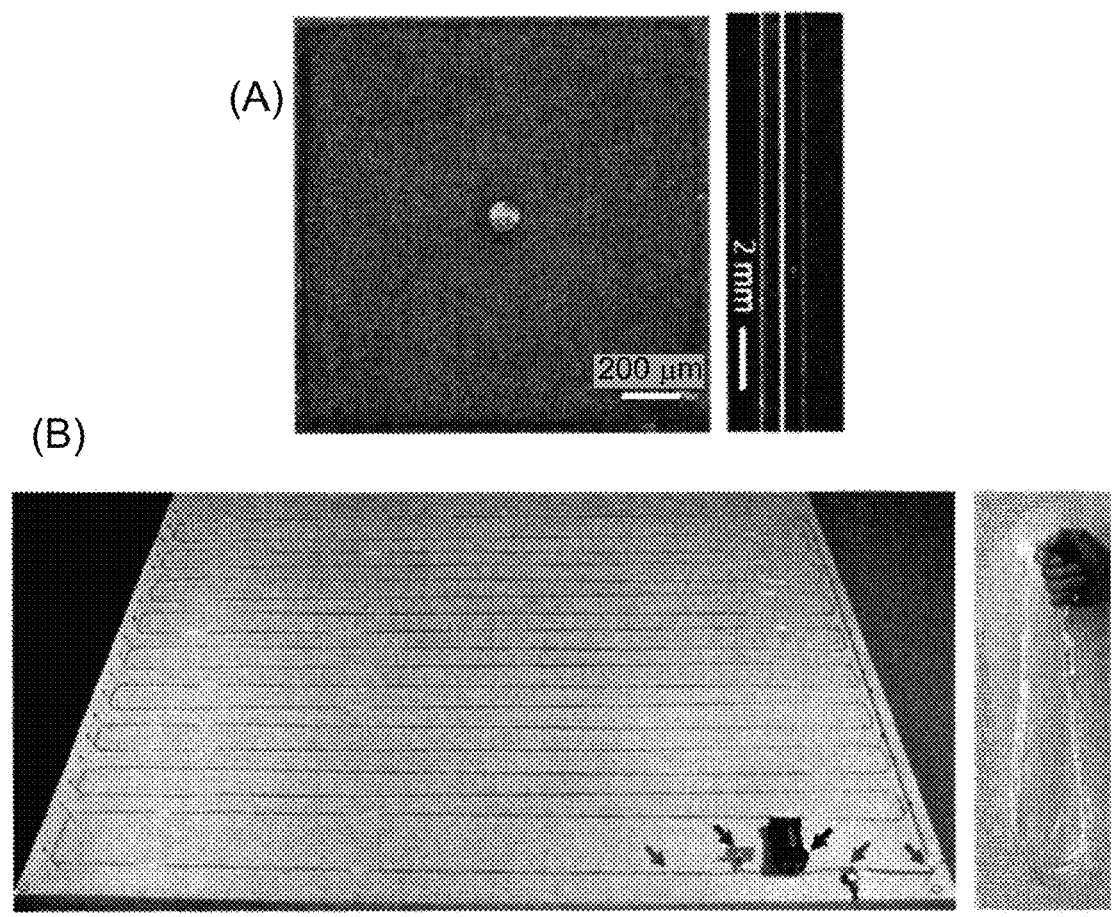
Figure 4F:
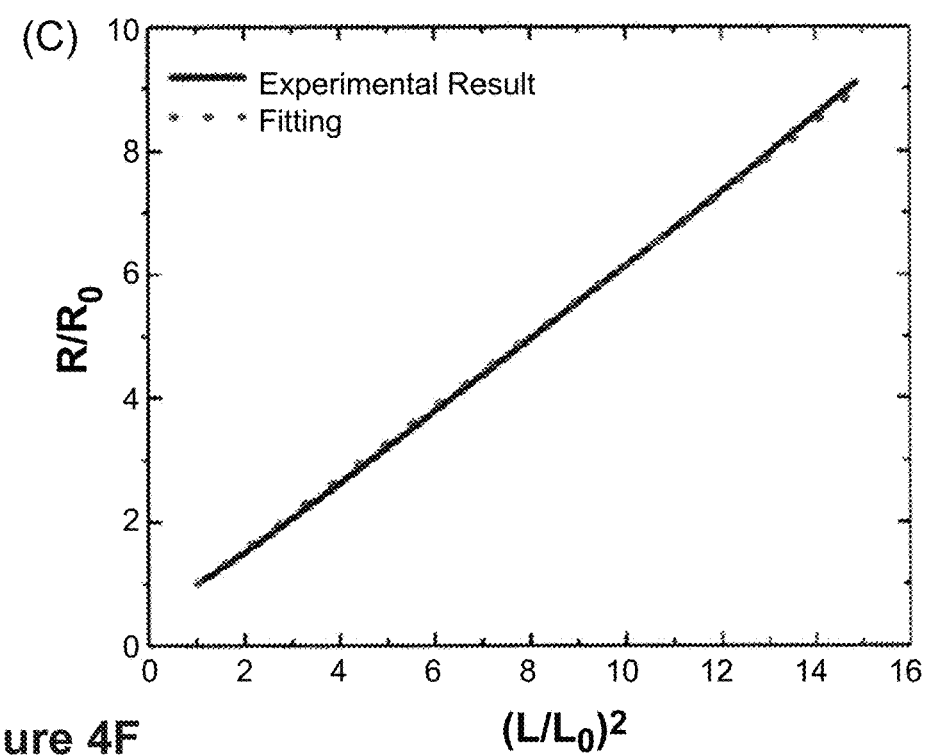
Figure 5A:
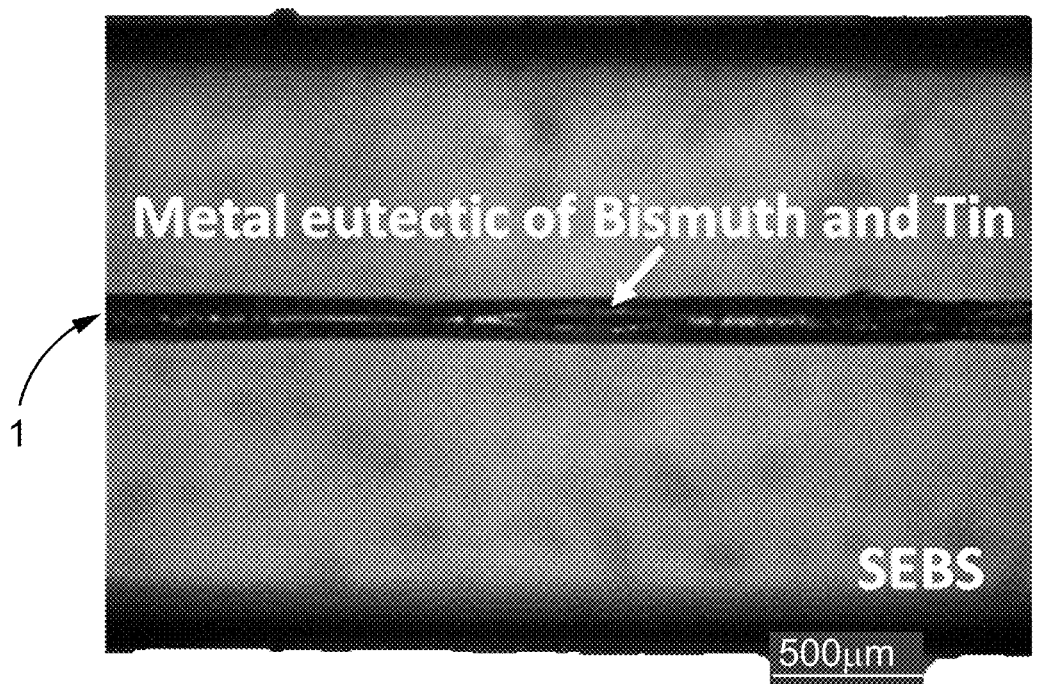
FIGS. 5A and 5B illustrate an example of SEBS fiber 1 with solid metal eutectic of Bismuth and Tin inside, that is a rigid material within a soft matrix.
Figure 5B:
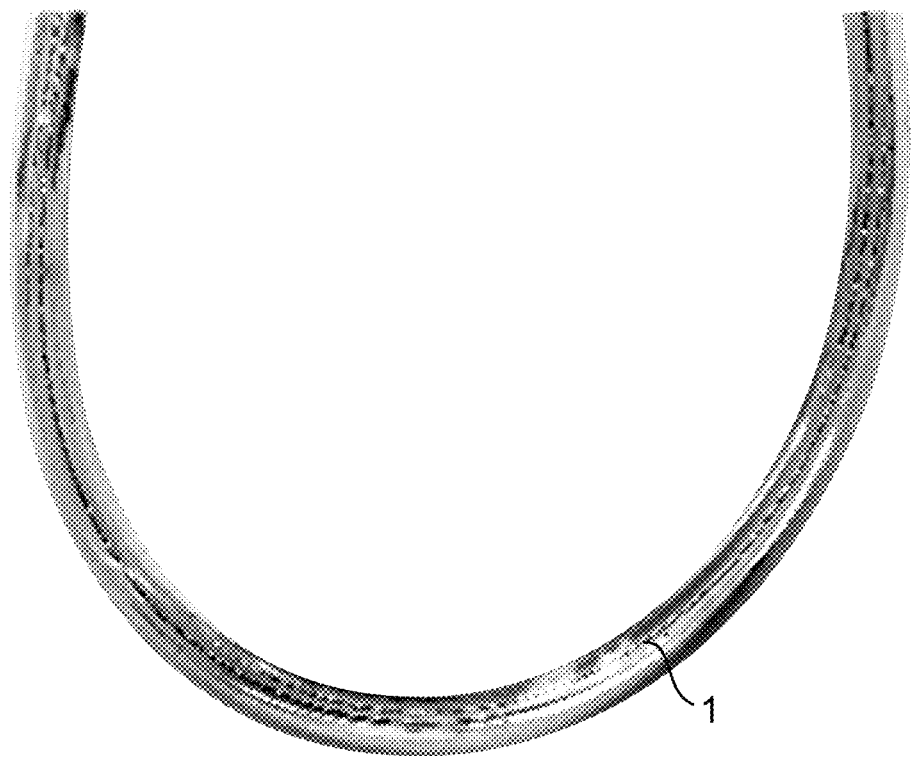

FIG. 2D to 2F illustrate a Transmission Electron Microscope (TEM) micrograph showing the microstructure of the preform 2 (FIG. 2D) and the drawn polymer 1 (FIGS. 2E and 2F). The structures are similar highlighting the fact that the thermal drawing process does not alter elastic properties of the polymer.

3. Making SEBS Preform with Hollow Channel Inside.

Channels may be fabricated via conventional milling or thermal embossing methods along the length direction in the surface of a preform 2. A solid rod such as steel or Teflon may then be inserted in the channel 3 and covered by another SEBS plate before consolidation under vacuum in an oven or inside a hot press. The rod is subsequently removed from the preform leaving a channel 3 of prescribed dimensions in the preform 2. Examples are illustrated in FIGS. 4A to 4D and 10A, 10B.

4. SEBS Preform with Integrated Liquid Metal Electrodes.

Liquid Gallium may be injected inside the hollow channels 3 previously fabricated in a SEBS preform 2. Alternatively, a solid Gallium rod may be inserted into the hollow channel(s) 3. Examples are illustrated in FIGS. 4A to 4F, and 13.

5. Bragg Mirror (Multi Layers) Fiber

Make different kind of TPE thin films via methods such as solution casting or hot press. Film thickness may be from several micron to hundreds of micron depending on requirement on the final thickness of different layers.

Stack different layers alternatively or stack different layers on an additional thick TPE plate, which may be used to support the thin films. Consolidate under heat and pressure.

Alternatively, different layers may be rolled around a cylinder (Teflon.) that is subsequently removed after consolidation. The multilayer structure is then thermally drawn into a fiber having a Bragg mirror structure with a size that depends on the draw-down ratio.

Example are given in FIGS. 12A to 12C.

6. Making Wavy Structure in TPE Fiber

A polycarbonate (PC) rod 8 is assembled into a SEBS preform 2, and the assembly in thermally drawn into a fiber 1 with a PC core 8. The fiber 1 is then stretched: the SEBS deforms elastically but the PC 8 quickly deforms plastically. When the pulling force is released, the SBES layer returns to its original length, while the PC rod 8 cannot and is forced to coil in order to comply with the original length. A PC helical structure 8 is obtained and may be deformed elastically, making the whole fiber 1 stretchable. The final fiber 1 may serve as stretchable light guide for example as a possible application. The fiber shows that the light intensity increases when the strain increases, see FIG. 9D. An example is illustrated in FIGS. 9A to 9D.

7. 4 Galinstan Channels in SEBS Fiber Surface

An SEBS plate, a CPE plate and a second SEBS plate with four cylindrical metal rods at its surface were pressed together under 0.02 bar for 15 min at 145° C. Then the metal rods were removed to obtain hollow channels 11 and filled with Galinstan. After thermal drawing, the CPE layer and the top SEBS layer were peeled off from the fiber. An SEBS fiber 1 with four Galinstan channels 11 at its surface was finally obtained.

An example is given in FIGS. 13, 15A and 15B.

8. Touch Sensing Fiber

Different component plates as described above were consolidated under 0.02 bar for 20 min at 145° C. The top two layers of SEBS and CPE were peeled off from the fiber after thermal drawing. The Geniomer was pulled out from the fiber end. Alternatively, tiny cuts (2 mm long) can also be made in the SEBS walls to pull out the Geniomer from the side.

Figure 17C:
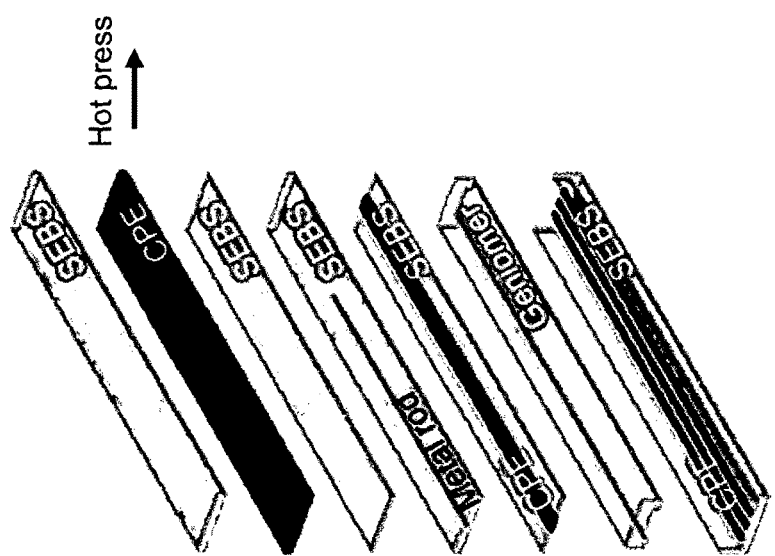

An example is illustrated in FIGS. 15A, 15B and 17. As illustrated in FIG. 17, the preform is made layer by layer (see FIG. 17A which indicates the properties of each layer and FIG. 17B), the steps followed being indicated as (a) to (e) in FIG. 17B and the drawn fiber 1 is shown in FIG. 17C and FIG. 15A (in cut-view).

9. SEBS (Sub)Micro-Channel-Patterned Optical Gratings Fiber

Micron-scale patterns with a period of for example 100 micron or 10 micron were first fabricated on an Si mask by photolithography. The initial patterns in the perform were made with a Heidelberg DWL200 laser writer on Cr-blank masks, then transferred to Si masks with a Suss MA6 mask aligner. The developed Si masks were then etched using a plasma etcher Alcatel AMS 200 SE to obtain the desired pattern depth. The etching depth was the same as the width of the structure, or half of the period, to obtain square shaped patterns, as an example of achievable structure. The Si masks were then molded onto a PDMS precursor via casting (PDMS 84 Dow-Coring) and curing at 80° C. to transfer the pattern onto a soft PDMS substrate. A PMMA plate was subsequently patterned by pressing it on the patterned PDMS at 1 bar for 10 min at 150° C. using a Thermal NanoImprinter EHN-3250. This PMMA plate was assembled with an SEBS plate and another PMMA plate (patterned or non-patterned) and hot-pressed (at pressure of 1 bar for 10 min at 150° C.) to get a preform. After thermal drawing the preform to create a fiber, the two PMMA layers were peeled off and the SEBS patterned optical grating fiber was obtained.

An example is illustrated in FIGS. 14A to 14C.

The embodiments of the invention described in the present application are only illustrative examples and should not be construed in any limiting manner. The present invention may also use equivalent means, materials and method steps to the ones described therein in the embodiments and examples with corresponding results. Also many different applications of the present invention may be envisaged as suggested hereabove, all within the scope of the present invention. It is also possible to combine different embodiments of the present invention according to circumstances and they are not exclusive.

Accordingly, the present description is neither intended nor should it be construed as being representative of the full extent and scope of the present invention. The present invention has been set forth in various levels of detail in the detailed description of the invention and no limitation as to the scope of the present invention is intended by either the inclusion or non inclusion of elements, components, etc. in the present description. Additional aspects of the present invention have become readily apparent from the detailed description, particularly when taken together with the drawings illustrating examples of the invention.

RELATED PATENTS AND SCIENTIFIC PUBLICATIONS

1. Kao, K. & Hockham, G. Dielectric-fibre surface waveguides for optical frequencies. Proc. Iee. 1151-1158 (1966). at <http://ieeexplore.ieee.org/xpls/abs_all.jsp?arnumber=5250060>
2. Russell, P. Photonic crystal fibers. *Science* 299, 358-62 (2003).
3. Abouraddy, A., Bayindir, M. & Benoit, G. Towards multimaterial multifunctional fibres that see, hear, sense and communicate. *Nat. Mater.* 6, (2007).
4. Tao G., Abouraddy A., Stolyarov A. M., Multimaterial fibers, *Inter. J. of Appl. Glass Science* 3 [4] 349-368 (2012)
5. "Optoelectronic Fiber Co-drawn from Conducting, Semiconducting, and Insulating Materials", U.S. Pat. No. 7,295,734 B2
6. "Optoelectronic Fiber Photodetector", U.S. Pat. No. 7,292,758 B2

The invention claimed is:

1. A thermal drawing method for forming a fiber comprising the steps of:
   providing a preform of a material for the fiber;
   heating the material such that the preform necks down under its own weight and produces a lower end; and
   continuously drawing a fiber from the lower end of the preform,
   wherein the material includes an elastomer.

2. The method as defined in claim 1, wherein the step of continuously drawing includes co-drawing the fiber with another material.

3. The method as defined in claim 1, further comprising the step of:
   providing an additional element to the preform before the step of continuously drawing, the additional element including at least one of a metallic electrode made of a conductive medium, a semiconducting material, an insulating material, and optical material, and a functional material.

4. The method as defined in claim 1, further comprising the steps of:
inserting a thin metallic wire in a channel of the fiber to form an embedded electrode; and
encapsulating a connection with the embedded electrode by an adhesive to improve mechanical resistance of the connection.

5. The method as defined in claim 1, wherein the material of the preform further includes nanoscale objects to bring functionality to the material.

6. The method as defined in claim 5, wherein the nanoscale objects include at least one of nanoparticles and nanotubes.

7. The method as defined in claim 1, wherein in the step of heating the material, a heating furnace provides a heating temperature to decrease the viscosity of the elastomer for deformation such that the material reaches an elastomeric phase before the preform is subjected to the step of continuously drawing.

8. The method as defined in claim 1, wherein the material further includes a thermoplastic thereby forming a thermoplastic elastomer (TPE) that has a thermoplastic domain that physically cross-links an elastomeric phase.

9. The method as defined in claim 8, wherein in the step of heating the material, a heating furnace provides a heating temperature to reach a softening temperature of the TPE before the preform is subjected to the step of continuously drawing.

10. The method as defined in claim 1, further comprising the step of:
attaching the lower end of the preform to a pulling system after the step of heating the material.

* * * * *